United States Patent [19]

Jackson et al.

[11] Patent Number: 4,884,013
[45] Date of Patent: Nov. 28, 1989

[54] MOTOR UNIT FOR A FLUID PUMP AND METHOD OF OPERATION

[75] Inventors: Edward Jackson, Northford; Joseph Pasqualucci, Seymour, both of Conn.

[73] Assignee: Sherwood Medical Company, St. Louis, Mo.

[21] Appl. No.: 144,795

[22] Filed: Jan. 15, 1988

[51] Int. Cl.⁴ .............................................. A61M 5/00
[52] U.S. Cl. .............................. 318/481; 128/DIG. 1
[58] Field of Search ................ 318/481; 128/DIG. 1, 128/DIG. 12, DIG. 13; 222/59, 63; 604/9, 30, 31, 65, 67, 120, 183, 186, 191, 257, 258

[56] References Cited

U.S. PATENT DOCUMENTS

| | | | |
|---|---|---|---|
| 3,230,767 | 1/1966 | Heigl et al. | 73/198 |
| 3,363,160 | 1/1968 | Morris | 318/341 |
| 3,364,410 | 1/1968 | Foreman | 318/443 |
| 3,389,325 | 6/1968 | Gilbert | 320/31 |
| 3,498,228 | 3/1970 | Blumle et al. | 222/644 |
| 3,527,220 | 9/1970 | Summers | 604/153 |
| 3,636,767 | 1/1972 | Duffy | 73/861.77 |
| 3,736,930 | 6/1973 | Georgi | 128/DIG. 13 X |
| 3,739,943 | 6/1973 | Wilhelmson et al. | 128/DIG. 13 X |
| 3,845,375 | 10/1974 | Stiebel | 318/463 |
| 3,873,814 | 3/1975 | Mirdadian | 377/21 |
| 3,985,133 | 10/1976 | Jenkins et al. | 128/DIG. 12 X |
| 4,016,468 | 4/1977 | Graf | 318/434 |
| 4,024,864 | 5/1977 | Davies et al. | 128/DIG. 13 X |
| 4,181,476 | 1/1980 | Malbec | 417/477 |
| 4,217,993 | 8/1980 | Jess et al. | 128/DIG. 13 X |
| 4,221,543 | 9/1980 | Cosentino et al. | 417/22 |
| 4,253,341 | 3/1981 | Ikeda et al. | 73/861.77 |
| 4,256,437 | 3/1981 | Brown | 417/45 |
| 4,275,727 | 6/1981 | Keeri-Szanto | 128/DIG. 13 X |
| 4,278,085 | 7/1981 | Shim | 128/DIG. 12 X |
| 4,299,218 | 11/1981 | Knigge et al. | 604/67 |
| 4,326,837 | 4/1982 | Gilson et al. | 417/12 |
| 4,385,630 | 5/1983 | Gilcher et al. | 604/35 X |
| 4,417,889 | 11/1983 | Choi | 128/DIG. 13 X |
| 4,444,546 | 4/1984 | Pazemenas | 417/12 |
| 4,447,191 | 5/1984 | Bilstad et al. | 417/12 |
| 4,469,481 | 9/1984 | Kobayashi | 128/DIG. 12 X |
| 4,487,604 | 12/1984 | Iwatschenko et al. | 128/DIG. 12 X |
| 4,492,531 | 1/1985 | Kenji et al. | 417/477 X |
| 4,498,843 | 2/1985 | Schneider et al. | 417/22 |
| 4,514,670 | 4/1985 | Fassel et al. | 318/467 |
| 4,515,584 | 5/1985 | Abe et al. | 417/477 X |
| 4,518,327 | 5/1985 | Hackman | 417/477 |
| 4,604,034 | 8/1986 | Wheeldon et al. | 417/18 |
| 4,613,327 | 9/1986 | Tegrarian et al. | 128/DIG. 12 X |
| 4,619,653 | 10/1986 | Fischell | 128/DIG. 13 X |
| 4,636,144 | 1/1987 | Abe et al. | 417/63 |
| 4,657,486 | 4/1987 | Stempfle et al. | 417/12 |
| 4,662,872 | 5/1987 | Cane | 128/DIG. 1 X |
| 4,676,776 | 6/1987 | Howson | 128/DIG. 13 X |
| 4,680,512 | 7/1987 | Melocik | 318/139 |
| 4,685,903 | 8/1987 | Cable et al. | 128/DIG. 12 X |
| 4,696,671 | 9/1987 | Epstein et al. | 604/67 |
| 4,756,706 | 7/1988 | Kerns et al. | 128/DIG. 13 X |
| 4,778,449 | 10/1988 | Weber et al. | 128/DIG. 13 X |

*Primary Examiner*—Bentsu Ro
*Attorney, Agent, or Firm*—Richard D. Allison; Andrew J. Beck; Charles Smith

[57] ABSTRACT

An enternal nutrition pump system operates in a cyclical manner with a period between cycles being selected in accordance with the desired fluid delivery rate. Each pump cycle may correspond to a single rotation of the rotor or a fractional rotation of the rotor. Rotor rotation may alternatively be sensed by utilization of magnetic sensors or by monitoring of the AC componenet of current supplied to a DC motor driving the rotor.

8 Claims, 4 Drawing Sheets

MOTOR UNIT FOR A FLUID PUMP AND METHOD OF OPERATION

BACKGROUND OF THE INVENTION

This invention relates to pumps for delivering medical fluids and particularly relates to peristaltic pumps for delivery of enteral nutrition fluids to a patient.

In accordance with known techniques the delivery of enteral nutrition fluids to a patient can be accurately controlled as to volumetric delivery rate by the use of a delivery system which includes a motor unit and a disposable delivery set. Likewise similar systems may be used for pumping of other fluids for medical purposes, such as intravenous infusion, blood pumping or supply of measured volumes of liquid medication to pre-loaded syringes or other containers.

In known systems for delivering enteral fluids the rate of fluid delivery is controlled by regulating the speed of a pump motor in accordance with the desired volume rate. Pump motor speed may be controlled, for example, by providing pulses to a stepper motor. Another system for providing variable rate fluid delivery makes use of a peristaltic pump with variable tension on the pump tube in combination with a constant speed motor.

In other known systems for pumping medical fluids there are provided means for monitoring rotation of the pump rotor, for example, by magnetic detection or by optical rotation detectors. In such systems the actual rotation rate of the motor is compared to the desired rotation rate for purposes of making corrections to the rotation rate of the motor. Alternately the motor may be operated to rotate the pump by a number of rotations corresponding to the desired volume.

It is an object of the present invention to provide a new and improved method for regulating the volumetric rate of fluid delivery in a medical fluid delivery system and to provide apparatus for carrying out the improved method.

SUMMARY OF THE INVENTION

In accordance with the present invention there is provided a motor unit for a medical fluid delivery system for use with a disposable delivery set for pumping medical fluid at a desired volumetric rate. The motor unit includes a pump operating means, including a motor for acting in cooperation with the delivery set to deliver a volume of the fluid during each operating cycle. There is further provided a pump control means for controlling the pump operating means to deliver the fluid at a desired volumetric rate. The pump control means includes means for activating the pump operating means for one of the operating cycles and for repeating the activation at variable time intervals which are selected in accordance with the selected volumetric rate.

In accordance with a preferred embodiment of the invention the pump operating means is a pump rotor for operating in connection with a pump tube on the delivery set to form a peristaltic pump and the pump operating cycle comprises a selected angular rotation of the pump rotor. In one arrangement the pump control means includes means for sensing the condition of the pump operating means with respect to an operating cycle, and the sensing means comprise a magnet and a magnetic field sensor. In another arrangement the sensing means may detect the AC component of the current supplied to a DC motor.

The medical fluid delivery system which comprises the novel motor unit and a disposable fluid delivery set carries out a novel method for controlling the rate of fluid delivery. The novel method includes providing means for detecting the completion of an operating cycle of the pump operating means and operating the motor unit until the completion of the operating cycle is detected. Operation of the motor unit is repeated at variable time intervals which are selected in accordance with the desired rate of fluid delivery.

In accordance with another aspect of the present invention the AC component of the DC motor current is detected and compared to a reference level in order to detect the current variation which results from the presence of a pump tube on the rotor. Accordingly, any mis-installation of the pump tube will be detected by the fluid delivery pump.

For a better understanding of the present invention, together with other and further objects, reference is made to the following description, taken in conjunction with the accompanying drawings, and its scope will be pointed out in the appended claims.

DESCRIPTION OF THE INVENTION

Figure 1:
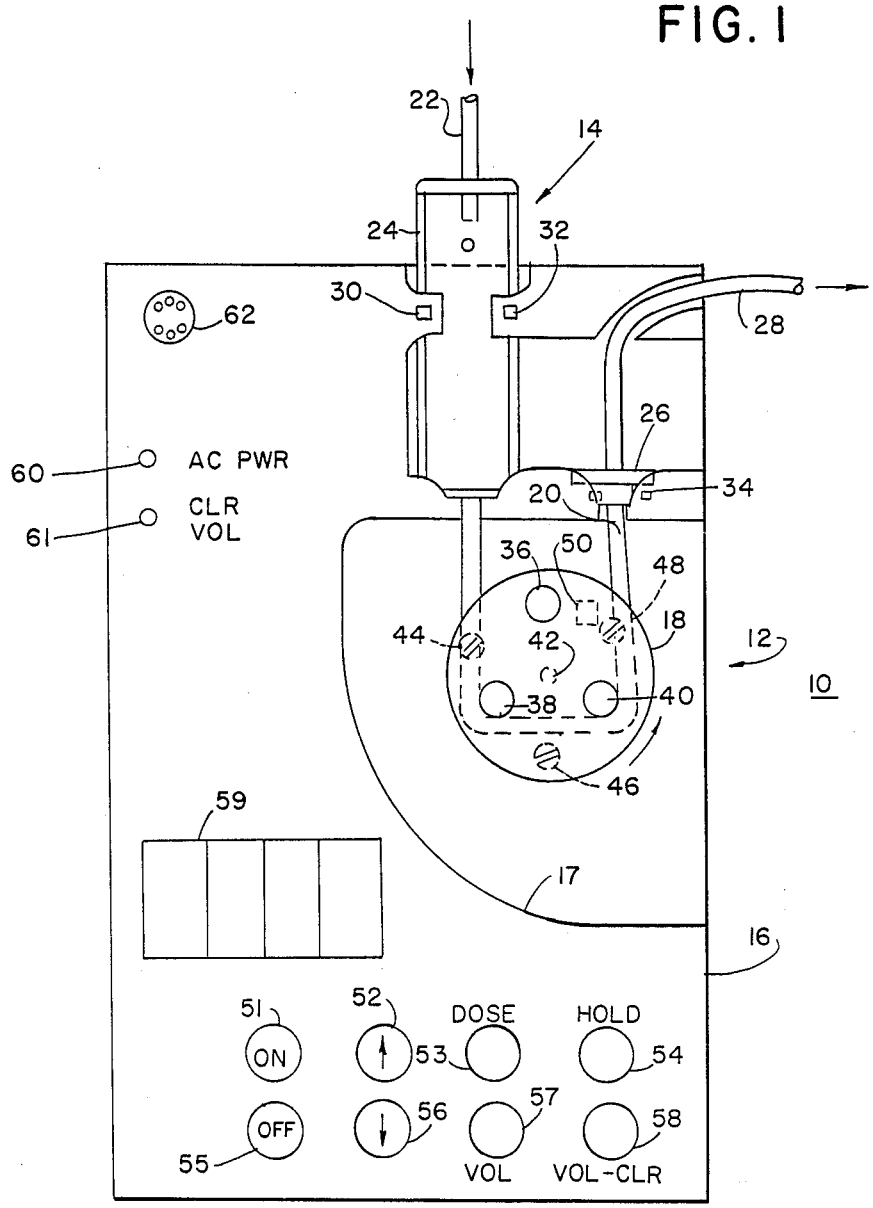
FIG. 1 is a plan elevation view of an enteral fluid delivery system incorporating the present invention.

FIG. 1 is an illustration of an enteral fluid delivery system incorporating a motor unit in accordance with the present invention. The enteral delivery system 10 includes a motor unit 12 and a disposable delivery set generally indicated as 14 which is arranged to be mounted on the motor unit. The motor unit 12 includes a housing 16, which in the illustrated embodiment includes a recess 17 within which a rotor 18 is mounted. Rotor 18 is driven by a conventional constant speed D.C. motor which drives shaft 42. The delivery set 14 includes a pump tube 20, made of flexible plastic which surrounds rotor 18 and interacts with 3 rollers 36, 38 and 40 mounted on rotor 18 to form a peristaltic pump. Rotation of the rotor 18 in the direction indicated by the arrow in FIG. 1 causes the rollers 36, 38 and 40 to interact with pump tube 20 and pump fluid through the tube at a rate which is determined by the rate rotation of rotor 18.

Delivery set 14 includes an inlet tube 22, which is connected to a supply of enteral fluids, such as a fluid reservoir which may be mounted on an IV pole above the motor unit 12. The inlet tube 22 is connected to drip chamber 24 which is mounted in a recess on housing 16 and secured to one end of pump tube 20. The outlet end of pump tube 20 is provided with a mounting member 26 which is received in another recess on housing 16 to thereby secure the outlet end of tube 20. A fluid delivery tube 28 is connected to mounting member 26 and supplies fluid pumped by the system to an enteral feeding tube connected to a patient or to another medical fluid delivery system.

The system illustrated in FIG. 1 additionally includes a light source 30 and a light detector 32 for operation in connection with drip chamber 24 to detect the occurrence of drops in the drip chamber which pass between light source 30 and detector 32 in a manner which is known in the art. Mounting member 26 includes magnetized material, the presence of which can be detected by magnetic field detector 34.

The motor unit 12 includes control buttons 51 through 58 for operating the unit to turn it on or off, to set the dose or volume rate of fluid delivery by the pump, to interrupt operation of the pump and to increase or decrease the designated fluid volume or volume rate. A four digit alphanumeric segment display 59 is provided for indicating the selected fluid delivery rate or delivered volume and for providing alarm messages or codes. Light emitting diode 60 and 61 are provided for indicating that the unit is plugged into AC power or indicating that the volume setting has been cleared. An enunciator 62 is provided for signalling an audible alarm to indicate, for example, that the pump has completed delivering a designated volume of fluid.

Housing 16 is provided with a magnetic field sensor 50 which is arranged adjacent and behind rotor 18 in order to detect the magnetic field provided by magnets 44, 46 and 48 which are mounted on rotor 18. The presence of the magnets 44, 46 and 48 is detected as the magnets pass sensor 50 during rotation of rotor 18.

Figures 1, 2:
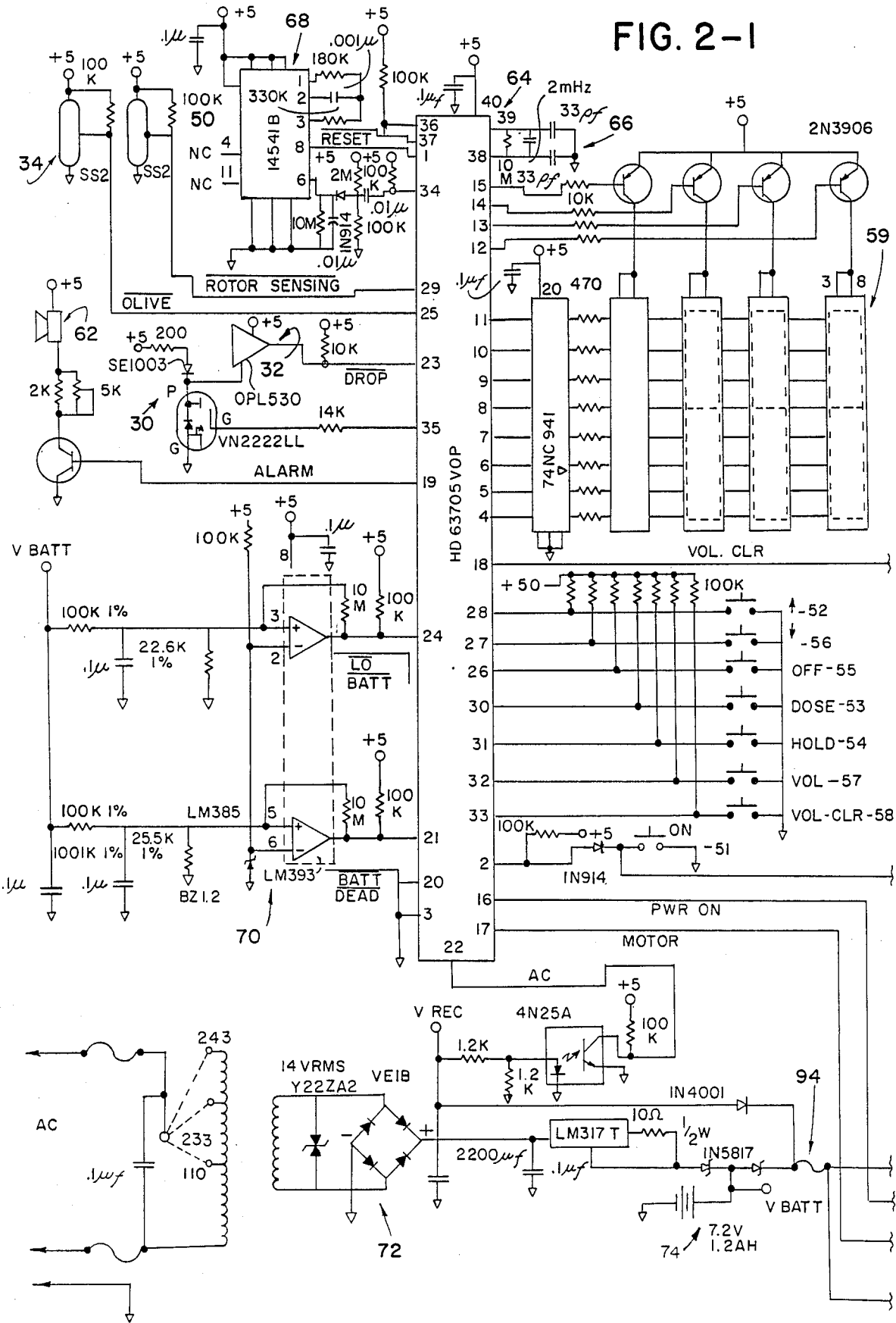
FIG. 2 is a circuit diagram for the system of FIG. 1.
Figure 2:
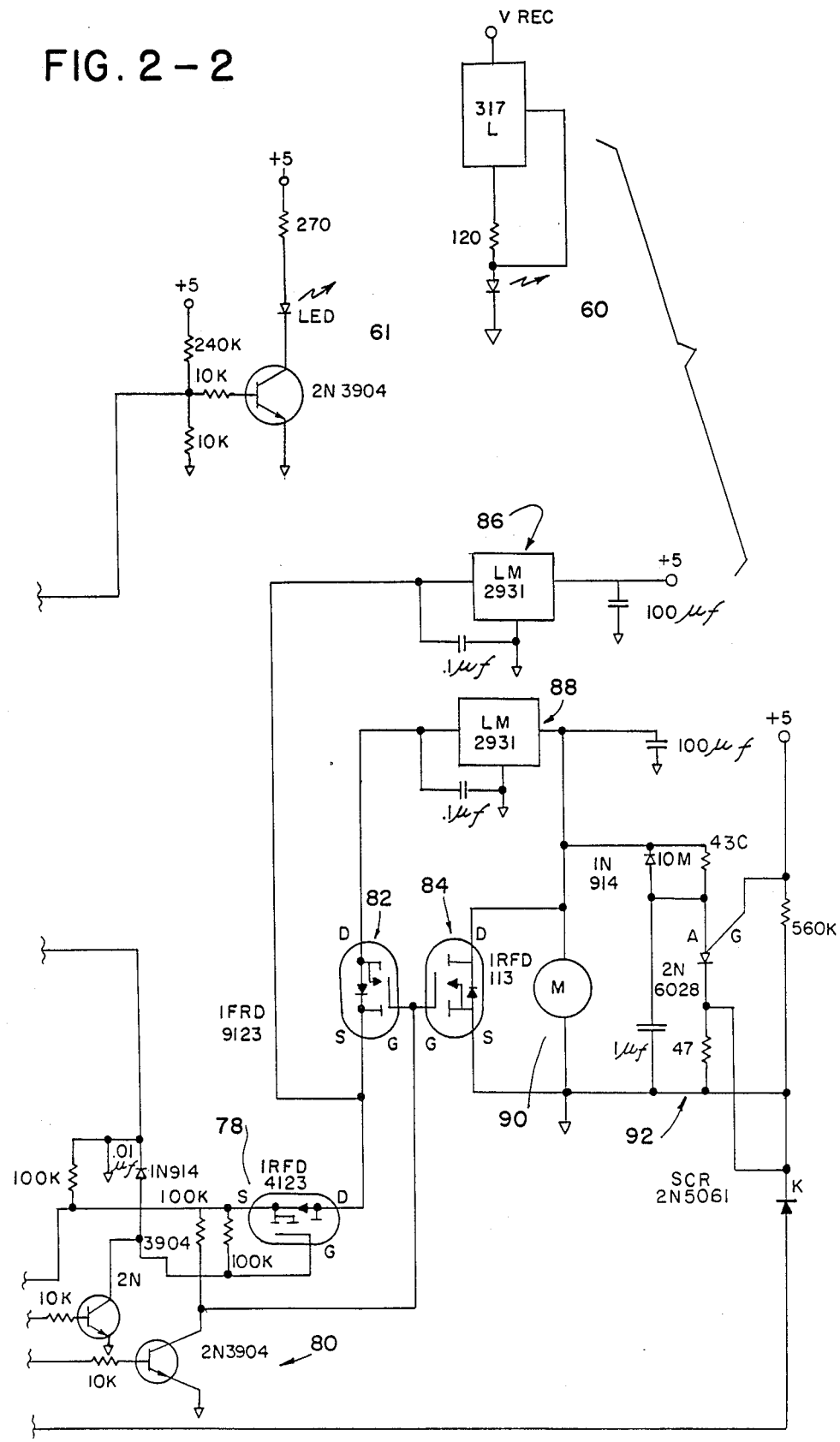

FIG. 2 is a schematic diagram of the circuits in the pump motor unit 12 of FIG. 1. The schematic representations of the various components of FIG. 1 have been given same reference numerals in FIG. 2.

The motor unit operates under the control of a microcomputer 64 which is provided with a control program which is set forth in Appendix I. A programmable interval timer 68 is provided for operating and initiating microcomputer 64. A clock 66, operating at 2 Mhz, provides clock pulses to the system. The various controls of the unit, 51 through 58, are provided as input signals which ground various input terminals of the microcomputer to thereby signal the operators input instructions. The alphanumeric display 59 is driven by the microcomputer as is LED indicator 61. Additional inputs to the microcomputer are provided by the magnetic field sensors 34 and 50 which sense respectively the magnetized mounting member 26 and the magnets 44, 46 and 48 on rotor 18. Likewise the drop detector 30, 32 is connected to provide input signals to the microcomputer. AN AC power rectifier 72 is provided for AC operation and battery charging. Portable DC operation is available using battery 74. The AC circuit is arranged to charge the DC battery when the unit is connected to AC power. A low battery and dead battery detector circuit 70 is provided to signal the microcomputer that the battery needs recharging. The microcomputer provides an output motor signal which is coupled by transistor 80 to switching transistors 82, 84. Transistor 82 turns on the power supply to motor voltage regulator 88 when the motor is to be operated and transistor 84 short circuits the motor to lock it into position when the motor signal is no longer present. Switching transistor 78, which is provided with a power signal by transistor 76, operates to supply current to the motor system and the other electronic systems by voltage regulator 86 when power is turned on. The motor 90 is provided with a safety circuit 92 which provides a short circuit when the motor is operated for an excess period of time. The short circuit causes fuse 94 to open thereby disabling the set when continuous motor operation occurs, to avoid providing excess enteral fluid to a patient.

Figure 4:
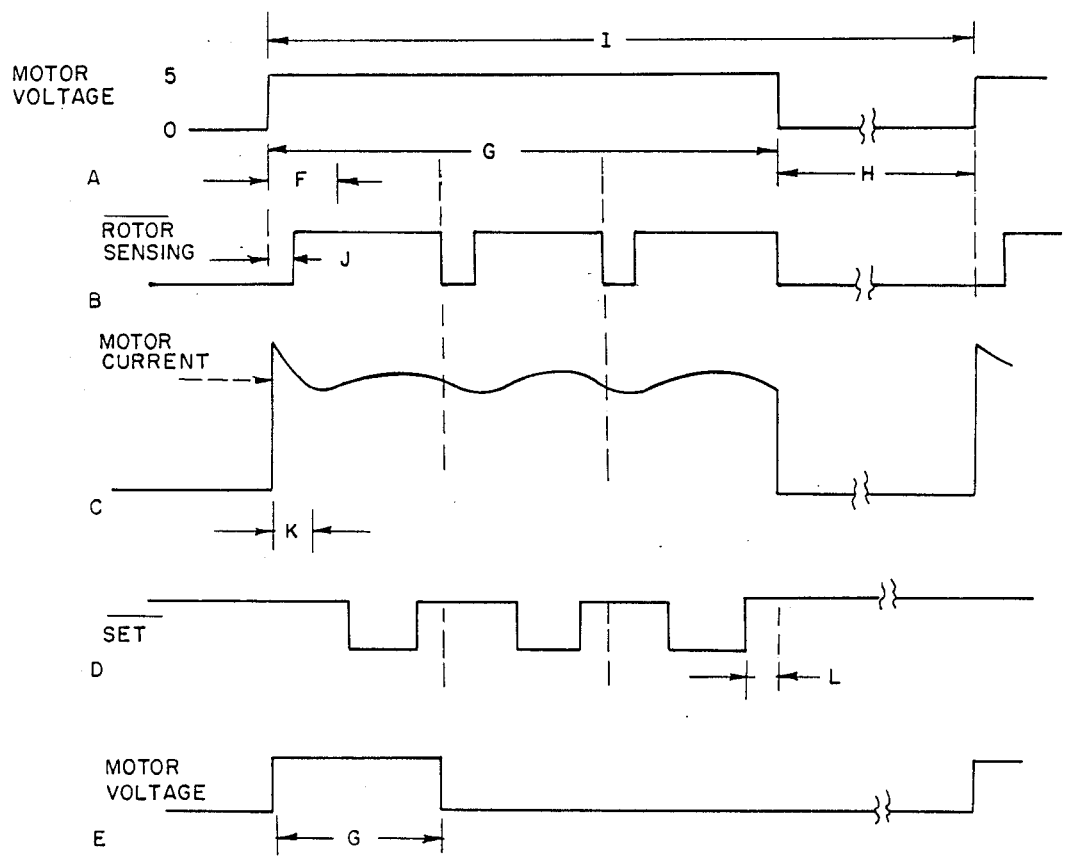
FIG. 4 is a timing diagram illustrating signals utilized in the present invention.

Unlike conventional enteral nutrition systems the system 10 of the present invention is designed to provide an intermittent motor operation with the periodicity of the intermittent operation being regulated to adjust to the desired rate of fluid delivery. The operation of the system of the present invention is therefore cyclical and will be explained with respect to timing diagrams of FIG. 4. Graph A of FIG. 4 illustrates the motor voltage of the enteral fluid delivery system 10. The motor voltage is turned on and operated for a time period G which is regulated by detecting the rotation of rotor 18, in the case of Graph A for one complete revolution. With reference to FIG. 1 it may be seen that during one complete revolution, represented by motor voltage period G, three magnets 44, 46 and 48 all pass magnetic field detector 50 and are sensed thereby. Curve B in FIG. 4 illustrates the output signal from the rotor sensing magnetic field detector 50 which occurs during the cycle of operation indicated by motor voltage G. During an initial period of approximately 0.45 seconds designated F in FIG. 4 the operation of the rotor sensing is inhibiting by software in microcomputer 64, so that the initial on period J of magnetic field detector 50 is not responded to by the program. Thereafter, during one complete revolution of the rotor, the signal from detector 50 goes to zero as each magnet is encountered by detector 50. Upon detection of the third magnet, at the end of period G, the motor voltage is turned off. In accordance with the preferred embodiment of the present invention the unit repeats the cyclical operation a time period I after initiation of the first operation. The time period H during which there is provided no motor voltage is permitted to be variable, since it depends on the actual time taken for rotation of the rotor and the selected interval I. The interval I is selected according to the rate of fluid delivery to be provided by the set which is set by the operator. In one embodiment of the invention period I varies from 13.5 seconds corresponding to a delivery rate of 100 milliliters per hour to 4.5 seconds corresponding to a fluid delivery rate of 300 milliliters per hour. Motor operation period G takes approximately 4 seconds but may vary according to mechanical conditions of the motor and pump tube.

Graph E in FIG. 4 shows an alternate timing arrangement wherein the motor cycle consists of a single one-third of a rotation of the rotor 18. In accordance with the operation method of Graph E the motor current period G' is ended by the detection of the first of the three circumferentially arranged magnets by magnetic field sensor 50. Again the timing I between each operating cycle of the motor is varied in order to control volumetric fluid rate delivered by the pump. In the same embodiment as previously discussed a fluid rate of 1 to 100 milliliters per hour can be delivered using a cycle interval I which ranges from 450 to 4.50 seconds.

Figure 3:
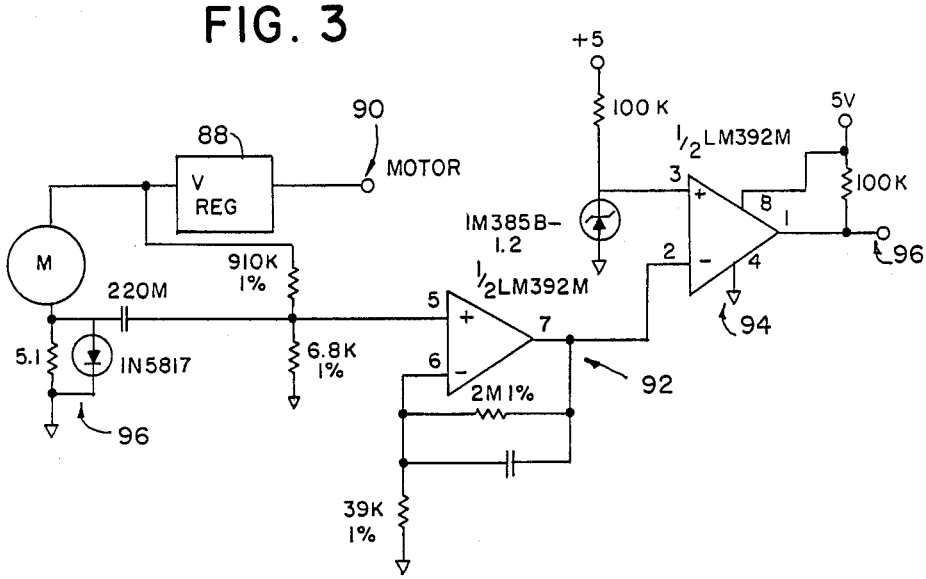
FIG. 3 is a circuit diagram for a portion of a modified delivery system in accordance with the present invention.

As an alternate, or in addition to providing magnets on rotor 18 for purposes of detecting completion of a motor cycle, the motor current may be monitored for purposes of determining the rotational position of the rotor 18. FIG. 3 is a schematic diagram of a circuit wherein there is provided a motor current monitoring circuit 96 which includes a low resistance resistor in series with the motor the voltage across which is AC coupled to an AC amplifier 92 for purposes of monitoring the AC component of the DC motor current. Graph C of FIG. 4 illustrates a typical motor current for the operating cycle of Graph A of FIG. 4. The motor current initially rises to a high level for purposes of overcoming the starting resistance and accelerating rotor 18 to its normal velocity. Thereafter the motor current drops but reaches periodic peaks corresponding to the resistance of rollers 36, 38 and 40 as they stretch pump tube 20 to its furthest position. The peak periods of motor current, which are illustrated as negative going pulses in the digitized signal of curve D, which is the output at point 96 of the circuit of FIG. 3, may be used for purposes of detecting rotor position and may be used also for assuring that the pump tube 20 is properly mounted to rotor 18. Because of the initially high rotor current, which results from starting up the rotor, the current sensing is software inhibited for time period K of approximately 0.25 seconds prior to initiating the threshold detection which results in the pulses of curve D. Each of the pulses illustrated in curve D, which are negative going, have a positive going pulse which occurs a time period L prior to the end of a motor cycle, there being three such pulses during one rotation of the rotor. Accordingly, the curve D signal can be used for purposes of detecting and monitoring rotation position of rotor 18, and thereby indicating to the motor control circuit the completion of an operating cycle. As an alternate to providing delay L after the end of the curve D pulses, the motor cycle may be arranged to end at the end of the pulse, providing a different rotor position between cycles.

The motor current monitoring previously described can additionally be used in cases wherein the motor voltage is provided only for a one-third rotation of the rotor as discussed with respect to curve E.

An additional use of the motor current monitoring circuit, which provides the signal of curve D of FIG. 4 is to provide assurance to the system that the pump tube 20 has been properly mounted on rotor 18. Accordingly at the initiation of motor current and after a delay period K a flag can be set by the microprocessor which is cleared by the negative going pulse of curve D to indicate proper pump tube positioning. The flag would be reset at the start of each operating cycle or may also be reset on the occurrence of the one-third rotation of the rotor sensing current shown by curve B. If the flag is not cleared by the negative going pulse of curve D there is an indication that either there is no pump tube or that the pump tube has been improperly mounted and an alarm signal can be initiated.

While there has been described what are believed to be the preferred embodiments of the present invention, those skilled in the art will recognize that other and further modifications may be made thereto without departing from the spirit of the invention and it is intended to claim all such changes and modifications as fall within the true scope of the invention.

"Copyright 1987
Sherwood Medical"

```
1       $CHIP(6305)
2       $pagewidth=132
3       $PAGINATE
4       $TITLE(K224/324 PUMP)
5       $XREF
6       ;=============================================================================
7       ;
8       ;       This file contains the software for the K224/K324 series of
9       ;       Enteral Feeding Pumps. It is based on COMB02.ASM a combined
10      ;       F1500 and K224 program. See COMB02.ASM for revision history.
11      ;
12      ;=============================================================================
13      ; FILE NAME= KPMP31.ASM
14      ;-----------------------------------------------------------------------------
15      ;  DATE    I REVISION I       DESCRIPTION
16      ;-----------------------------------------------------------------------------
17      ;
18      ; 12/04/87 I  031.0  I  DISPLAY LEADING ZERO'S IN DOSE MODE.
19      ;          I         I  CHECK FOR DROPS CONTINUOSLY IN RUN MODE
20      ;          I         I  WHEN RATE IS ( 100 ML/HR.
21      ;-----------------------------------------------------------------------------
22      ;
23      ; 11/24/87 I  030.0  I  ADD NOPS TO IR TEST DURING TESTD.
24      ;          I         I  CLEAR TESTD FLAG WHEN OFF MODE IS ENTERED TO
25      ;          I         I  ALLOW PUMP TO DISABLE IF NECESSARY.
26      ;          I         I  CLEAR VOL MODE FLAG WHEN LO BAT IS ENTERED
27      ;          I         I  LOCK-OUT HOLD/START AND VOL BUTTONS WHEN
28      ;          I         I  INC OR DEC BUTTONS ARE PRESSED.
29      ;          I         I  FIX CLR VOL LED ERROR
30      ;          I         I  CHECK DEC BUTTON BEFORE INC BUTTON.
31      ;          I         I  ADD DELAY TO INC AND DEC BUTTON IN DOSE MODE TO
32      ;          I         I  ALLOW TIME FOR doSE DISPLAY.
33      ;-----------------------------------------------------------------------------
34      ;
35      ; 11/11/87 I  029.0  I  CHANGE PUMP ID FROM PORTD(1), TO PORTB(6).
36      ;-----------------------------------------------------------------------------
37      ;
38      ; 10/23/87 I  028.0  I  FIXED 24 HOUR TIME ERROR. PUMP WAS TIMING 21 HOURS
39      ;          I         I  MODIFIED SO THAT PUMP DISABLES AFTER 24 HOURS
40      ;          I         I  WHEN ON AC OR BATTERY POWER.
```

```
;-----------------------------------------------------------------
;
; 10/16/87 |  027.0 | CHANGED SETCK ROUTINE TO TEST FOR SET WHENEVER
;          |        | PUMP IS IN RUN MODE. OLD VERSION ONLY CHECKED
;          |        | WHEN MOTOR IS RUNNING.
;          |        | RATE CHECK FOR 324 IS DISABLED DURING TEST MODE.
;          |        | DISABLE DOSE BUTTON WHILE INC OR DEC BUTTONS
;          |        | ARE PRESSED.
;-----------------------------------------------------------------
;
; 10/13/87 |  026.0 | ADD RECHECK OF PUMP ID DURING TESTD
;          |        | ADDED DELAY FROM MOTOR TURN-ON TO DEAD BAT ROUTINE
;          |        | CHANGED LOW BAT ROUTINE SO IT KILLS POWER IF
;          |        | LO BAT OCCURS WHEN UNIT IS ALREADY OFF.
;          |        | CHANGE POLARITY OF AC DETECT LINE. (REV 7 BOARD)
;-----------------------------------------------------------------
;
; 10/13/87 |  025.0 | CORRECTED ERROR IN 1/2 SEC TIMER.
;          |        | ADDED DOSE DEL CHECK PRIOR TO RUN MODE
;-----------------------------------------------------------------
;
; 10/12/87 |  024.0 | ADD NOPS IN DROPCK BETWEEN IR TURN-ON AND
;          |        | TEST TO ALLOW FOR SETTLING.
;          |        | SHORTED IR ON TIME.
;          |        | MOVE DROPCK FROM 8 MS TO 2 MS TO IMPROVE
;          |        | DROP DETECTION.
;-----------------------------------------------------------------
;
; 10/10/87 |  023.0 |  DEL STOP INSTR. FROM EACH DISABLE ROUTINE.
;          |        |  BLANK ALL DIGITS IN EACH DISABLE ROUTINE.
;-----------------------------------------------------------------
;
; 10/07/87 |  022.0 | THE RESET ROUTINE HAS BEEN MODIFIED TO KEEP
;          |        | THE PUMP OFF. TURN-ON IS NOW ACCOMPLISHED IN
;          |        | THE INT ROUTINE. CHANGE WAS MADE TO PREVENT STRAY
;          |        | RESEST SIGNALS FROM WATCHDOG FROM ACCIDENTLY
;          |        | TURNING PUMP ON DURING DISABLE SEQUENCE.
;-----------------------------------------------------------------
; 9/29/87  |  021.0 | REVISED THE DISABLE ROUTINES TO DISABLE INT
;          |        | AND LOOP UNTIL POWER DISSIPATES.
;
;
; 9/22/87  |  020.0 | TEST ROUTINE HAS BEEN ADDED. IT IS INITIATED BY
;          |        | PRESSING THE OFF AND HOLD BUTTONS DOWN AT THE
;          |        | SAME TIME FOR APPROX. 3 SEC WHEN PUMP IS OFF.
;
; 9/22/87  |  019.0 | MOTOR CONTROL SIGNAL POLARITY HAS BEEN REVERSED
;          |        | AND TEST MODE WAS CHANGED SO THAT CLR VOL LED
;          |        | IS TURNED OFF WHEN BUZZER IS.
;
; 9/08/87  |  018.0 | THE INCREMENT AND DECREMENT KEYS HAVE BEEN
;          |        | REVERSED TO COMPENSATE FOR PC BOARD R4.
;-----------------------------------------------------------------
;
; 9/03/87  |  017.0 | THIS PROGRAM HAS BEEN MODIFIED TO RUN ON A 2 MHZ
;          |        | CLOCK.
;          |        | THE LOW BAT TIME HAS BEEN SET TO 15 MIN.
;-----------------------------------------------------------------
;-----------------------------------------------------------------
;
; 8/28/87  |  016.0 | THE CLEAR DOSE FEATURE HAS BEEN DELETED
;-----------------------------------------------------------------
;
; 8/28/87  |  015.0 | THE HOLD ROUTINE HAS BEEN MODIFIED TO OCCUR
;          |        | 2 1/2 MIN FROM LAST BUTTON PRESSED.
;          |        | A WAIT STATEMENT HAS BEEN ADDED TO THE MAIN LOOP
;          |        | AND OFF LOOP ROUTINES.
;-----------------------------------------------------------------
; 8/21/87  |  014.0 | THIS VERSION HAS BEEN MODIFIED TO ACCOMADATE
;          |        | THE NEW ENCODED ROTARY SWITCH.
;          |        | THE HOLD AND INCREMENT BUTTONS HAVE BEEN SWITCHED
;          |        | TO SIMPLIFY THE RATE KNOB DECODE OPERATION.
;-----------------------------------------------------------------
;
; 8/12/87  |  013.0 | THIS VERSION HAS BEEN REDUCED BY CONVERTING
;          |        | THE RATE INCREMENT ROUTINES TO BINARY WITH
;          |        | DECIMAL ADJUST ADDING.
;-----------------------------------------------------------------
;
; 8/05/87  |  012.0 |  BLINK SUBROUTINE WAS MODIFIED SO THAT ONLY 3
;          |        |  DIGITS ARE ACTIVE WHEN PUMP IS 224.
;-----------------------------------------------------------------
;
```

```
; 7/30/87  | 011.0 | MODIFIED SO THAT VOLUME AND DOSE CAN BE CLEARED
;         |       | WITH CLR V/D BUTTON WHILE PUMP IS RUNNING.
;         |       | THE DISPLAY HAS BEEN CHANGED TO EYE ERR IF
;         |       | THE IR SENSOR IS BLOCKED DURING TEST SEQUENCE.
;---------------------------------------------------------------
;
; 7/25/87  | 010.0 | MODIFY DOSE DEL ERROR, SO THAT PRESSING HOLD
;         |       | BUTTON ONCE DISABLED ALARM AND MESSAGE. THIS
;         |       | WILL ALLOW THE USER TO UPDATE DOSE OR VOLUME
;         |       | WITH THE NEXT KEY STROKE.
;---------------------------------------------------------------
;
; 7/21/87  | 009.0 | modified to display DP scroll when motor on
;         |       | in LOW BAT state.
;---------------------------------------------------------------
;
; 7/16/87  | 008.0 | MODIFY HOLD BUTTON OPERATION FOR LO BAT STATE.
;         |       | WHEN HOLD PRESSED, ALARM STOPS AND MOTOR STOPS.
;---------------------------------------------------------------
;
; 7/13/87  | 007.0 | ADD NO SET FEATURE.
;         |       | MODIFY VOLUME DISPLAY. ADD SHORTED MOTOR SENSOR
;         |       | DETECTION SOFTWARE. MODIFY 24 HR TIME ROUTINE
;         |       | TO CLEAR VOL DELIVERED, BUT NOT TO KILL POWER.
;---------------------------------------------------------------
; 7/10/87  | 006.0 | FIX HIGH RATE ERROR BUG. MODIFIY LOW BAT TO
;         |       | CONTINUE TO RUN MOTOR WITH ALARM.
;---------------------------------------------------------------
;
; 7/08/87  | 005.0 | TRY NEW INCREMENT METHOD FOR DOSE.
;         |       | SAVES APPROX. 40 BYTES. ADDED LOW BAT TIMER,
;         |       | AND DEAD BAT SIGNAL.
;---------------------------------------------------------------
;
; 7/07/87  | 004.0 | 324 RATE INCREMENT CHANGED TO 5 ML FOR RATES
;         |       | GREATER THEN 50.
;---------------------------------------------------------------
;         |       |
; 6/29/87  | 003.0 | DOSE FEATURE IS ADDED. CURRENT SENSE SOFTWARE FOR
;         |       | SET DETECTION DELETED.
;         |       |
;---------------------------------------------------------------
; 6/25/87  | 002.0 | RATE INITIALIZED TO 0 ON POWER UP AND
;         |       | TURN-ON. WRAP AROUND OF DISPLAY REMOVED.
;
;---------------------------------------------------------------
;         |       |
; 6/01/87  | 001.0 | FIRST PUMP VERSION SEPARATED
;         |       | FROM COMBO2.ASM
;
$EJECT
;================================================================
;
;
;          PORT ASSIGNMENTS              A   ALL OUTPUTS
;
;
;----------------------------------------------------------------
; 7       6       5       4       3       2       1       0
; DP     /SEG g  /SEG f  /SEG e  /SEG d  /SEG c  /SEG b  /SEG a
;----------------------------------------------------------------
;
;
;                                         B   ALL OUTPUTS
;
;
;----------------------------------------------------------------
; 7       6         5      4        3        2        1        0
; BUZZER  VOL CLR   5VA    POWER   /DIGIT 4 /DIGIT 3 /DIGIT 2 /DIGIT 1
;         PMPID 1=224 1=ON ON/OFF  (324)
;----------------------------------------------------------------
;
;
;                                         C   ALL INPUTS
;
;
;----------------------------------------------------------------
; 7       6       5       4       3       2       1       0
; F1500/  AC/DC   /DROP   /LO BAT  /SET    /OFF    /B      /A
; PUMP                                             DOWN    UP
;----------------------------------------------------------------
;
;
```

```
                                                              D  0,1,2,3,4, INPUTS
                                                                 5,6 OUTPUTS
         ;  ------------------------------------------------------------
         ;    7        6       5       4        3        2       1       0
         ;    NC     IR-LED    NC    CLEAR    VOLUME   /HOLD   /DOSE    1/3
         ;           ON/OFF                                             REV
         ;  ------------------------------------------------------------
         ;

$EJECT
                 DEFSEG ABSLSEG,ABSOLUTE
                 SEG ABSLSEG
         ;
         ;
         ;************** SET UP RAM/ROM AND PORT ADDRESSES *********************
         ;
         USRRAM  EQU    $40       ;STARTING ADDRESS OF USER RAM.
         USRROM  EQU    $1000     ;STARTING ADDRESS OF USER ROM.
         PMPTST  EQU    $1C00     ;STARTING ADDRESS OF PUMP TEST SOFTWARE.
         ;
         PORTA   EQU    $00       ;PORT A DATA.
         PORTB   EQU    $01       ;PORT B DATA.
         PORTC   EQU    $02       ;PORT C DATA.
         PORTD   EQU    $03       ;PORT D DATA.
         ;
         DDRA    EQU    $04       ;PORT A DATA DIRECTION REGISTER.
         DDRB    EQU    $05       ;PORT B  "          "       "
         DDRC    EQU    $06       ;PORT C  "          "       "
         DDRD    EQU    $07       ;PORT D  "          "       "
         TDR     EQU    $08       ;TIMER DATA REGISTER.
         TCR     EQU    $09       ;TIMER CONTROL REGISTER.
         MISC    EQU    $0A       ;MISCELLANEOUS REGISTER
         ;
         ;        ****************************************************************
         ;                       EQUATES
         ;        ****************************************************************
         ;
         TABLE1  EQU    $101C
         TABLE5  EQU    $1000
         ;
         TIMEST  EQU    $02
         ;
         T8MS    EQU    $03
         T33MS   EQU    $03
         T1S     EQU    $0F                  ;1/2 SEC TIME CONSTANT
         T6M     EQU    $02                  ;(02 + 1) =  03 x 2.0 = 6 MINUTES
         T142S   EQU    $EF                  ;(EF + 1) = 240 x 0.5 = 2 MINUTES
         ;
         ;
         ;*************** INTERRUPT/RESET VECTOR TABLE *************************
         ;
                 ORG    $1FF4
         ;
                 DW     RESET     ;SERIAL INTERUPT TIMER 2
                 DW     TIMINP    ;TIMER INTERRUPT VECTOR (WAIT STATE)
                 DW     TIMINP    ;TIMER INTERRUPT VECTOR
                 DW     ONPOW     ;EXTERNAL INTERRUPT VECTOR
                 DW     ONPOW     ;SOFTWARE INTERRUPT VECTOR
                 DW     RESET     ;RESET VECTOR
         ;
         ;
         $EJECT
         ;
         ;*************** DEFINE VARIABLES IN USER RAM AREA *******************
         ;
         ;
                 ORG    USRRAM
         ;
         TS      DB     0         ;READING OFF BRIDGE BEFORE RISE BEGINS (AMBIENT)
         T5      DB     0         ;READING FROM AMP  5  SECOND AFTER BRIDGE RISE.
         T10     DB     0         ;         "       10
         T15     DB     0         ;         "       15
         T20     DB     0         ;         "       20
         T25     DB     0         ;         "       25
         ;
         ALGO    DB     0
         ;
         TIMLO   DB     0         ;LOWER BYTE OF 5 MINUTE DOWN COUNTER.
         TIMHI   DB     0         ;UPPER  "    "    "    "     "
         ;
         BATTM1  DB     0         ;15 MIN BATTERY TIMERS
```

```
004A 00              290        BATTM2  DB      0
                     291        ;
004B 00              292        HLDTM1  DB      0               ;HOLD TIME COUNTERS: 2 1/2 MIN
004C 00              293        HLDTM2  DB      0
                     294        ;
004D 00              295        SAMPL1  DB      0               ;STORAGE FOR THE LAST 5 A-TO-D READINGS.
004E 00              296        SAMPL2  DB      0               ;(SAMPL5 IS THE MOST RECENT).
004F 00              297        SAMPL3  DB      0
0050 00              298        SAMPL4  DB      0
                     299        ;
0051 00              300        DSPDG1  DB      0               ;7-SEGMENT DATA FOR LSD. (BIT 7 IS BACKPLANE CLOCK)
0052 00              301        DSPDG2  DB      0               ;"      "       "       " DIG 2.
0053 00              302        DSPDG3  DB      0               ;"      "       "       " DIG 3. (BIT 7 IS POWER CONTROL)
0054 00              303        DSPDG4  DB      0               ;"      "       "       " MSD. (BITS 7-3 ARE A/D CONTROL)
                     304        ;
                     305        ;
                     306        ;
0055 00              307        DS1     DB      0       ;CONTAINS FIRST TWO DIGITS OF DOSE
0056 00              308        DS2     DB      0       ;CONTAINS LAST TWO DIGITS OF DOSE
                     309        ;
                     310        ;       DS1 AND DS2 ARE TRANSFERRED TO SAMPL1-SAMPL4 BY BCDEXP
                     311        ;       ROUTINE.
                     312        ;
0057 00              313        DOSECT  DB      0       ;COUNTER FOR TIME IN DOSE MODE
                     314        ;
                     315        ;       VS1 AND VS2 ARE TRANSFERRED TO SAMPL1-SAMPL4 BY BCDEXP
                     316        ;
0058 00              317        DECML1  DB      0       ;FRACTION OF 1ML-IN VOLUME
0059 00              318        VS1     DB      0       ;CONTAINS FIRST TO DIGITS OF VOLUME
005A 00              319        VS2     DB      0       ;CONTAINS LAST TO DIGITS OF VOLUME
                     320        ;
005B 00              321        REG1    DB      0       ;TEMPORARY STORAGE
                     322        ;
005C 00              323        REG2    DB      0       ;        "
                     324        ;
005D 00              325        DRCNT1  DB      0       ;DROP COUNTERS
005E 00              326        DRCNT2  DB      0
                     327        ;
005F 00              328        REG3    DB      0       ;        "
0060 00              329        REG4    DB      0       ;        "
0061 00              330        REG5    DB      0       ;        "
                     331        ;
                     332        ;
                     333        ;
                     334        ;
0062 00              335        COUNT1  DB      0       ;GENERAL PURPOSE COUNTER REGISTER.
0063 00              336        COUNT2  DB      0       ;   "       "       "       "
0064 00              337        COUNT3  DB      0       ;   "       "       "       "
                     338        ;
                     339        ;************ REGISTERS AND VARIABLES USED DURING PREDICTION ************
                     340        ;
                     341        ;
0065 00              342        XH      DB      0       ;ARGUMENT STORAGE FOR 16-BIT MATH ROUTINES.
0066 00              343        XL      DB      0       ;                       "
0067 00              344        QH      DB      0       ;                       "
0068 00              345        QL      DB      0       ;                       "
0069 00              346        PH      DB      0       ;                       "
006A 00              347        PL      DB      0       ;                       "
                     348        ;
006B 00              349        TEMPA   DB      0
006C 00              350        TEMPX   DB      0
                     351        ;
006D 00              352        PSTAT1  DB      0       ;FIRST PUMP STATUS BYTE
                     353        ;                               0=HOLD    1=Unit on hold
                     354        ;                               1=MOTOR   1=Motor on
                     355        ;                               2=ON      1=Unit on
                     356        ;                               3=START   1=Unit in start mode
                     357        ;                               4=DISPLAY 1=Display on
                     358        ;                               5=CW      1=Clock wise rate change
                     359        ;                               6=CCW     1=Counter clock wise rate change
                     360        ;                               7=MODEL   1=324 0=224 Model
                     361        ;
                     362        ;
006E 00              363        PSTAT2  DB      0       ;SECOND PUMP STATUS BYTE
                     364        ;
       =006E         365        LOWBAT  EQU     PSTAT2  0=BATTERY 1=Low battery
       =006E         366        ACON    EQU     PSTAT2  1=AC      1=AC ON
       =006E         367        NDROP   EQU     PSTAT2  2=FLOW    1=Drop error
       =006E         368        HOLDER  EQU     PSTAT2  3=HOLD    1=Hold error
       =006E         369        NOSET   EQU     PSTAT2  4=SET     1=No set error
       =006E         370        ALRM    EQU     PSTAT2  5=ALARM   1=Audio alarm on
       =006E         371        VOLM    EQU     PSTAT2  6=VOLUME  1=Volume mode
       =006E         372        ERRON   EQU     PSTAT2  7=ERROR   1=Error mode
```

```
006F 00      373                  ;
             374       TSTERR  DB      0         ;B0 IS TEST ERROR FLAG
             375                                 ; SET IF EYES BLOCKED DURING TEST
             376                  ;
0070 00      377       DOSER   DB      0         ;DOSE DELIVIRED FLAG B0=1: DOSE DEL
0071 00      378       DFLAG   DB      0         ;DOSE MODE FLAG
             379                  ;                  B0= DOSE    1=DOSE MODE ON
             380                  ;                  B1= DTEST   1=DOSE BUTTON PRESSED
             381                  ;                                  LAST CYCLE, USED FOR
             382                  ;                                  DEBOUNCE.
             383                  ;                  B2= ZERO    1=DISPLAY ZERO
             384                  ;
0072 00      385       LTEST   DB      0         ;MAGNET LOW COUNTER, USED TO CHECK IF SENSOR
             386                                 ;IS STUCK LOW. INCREMENTED AS LONG REV SIGNAL
             387                                 ;IS LOW. CLEARED WHEN SIGNAL GOES HIGH.
0073 00      388       HTEST   DB      0         ;B0 - TEST FLAG FOR HOLD DEBOUNCE
             389                  ;              ;B1 - TEST FLAG FOR CLR VOL DEBOUNCE
0074 00      390       ZEROST  DB      0         ;ZERO STATUS FLAG
             391                                 ; B5 = 1 : DISPLAY IS ZERO
             392                                 ; B6 = 1 : MSD IS ZERO
             393                                 ; B7 = 1 : MSD-1 IS ZERO
             394                  ;
0075 00      395       VFLAG   DB      0         ;VOLUME DISPLAY TEST FLAG. SET WHEN 'VOL'
             396                                 ;IS DISPLAYED.
0076 00      397       CWF     DB      0         ;CLOCKWISE FLAG
0077 00      398       CCWF    DB      0         ;COUNTER CLOCKWISE FLAG
0078 00      399       SPEED1  DB      0         ;ROLL UP/DOWN SPEED
0079 00      400       VOLTIM  DB      0         ;VOLUME MODE ON TIMER
007A 00      401       THIRD1  DB      0         ;1/3 REV COUNTER
007B 00      402       THIRDR  DB      0         ;1/3 REV COUNTER
007C 00      403       OUTSPD  DB      0         ;SCROLLING SPEED COUNTER
007D 00      404       MOTIM1  DB      0         ;FIRST MOTOR TIME COUNTER
007E 00      405       MOTIM2  DB      0         ;SECOND MOTOR TIME COUNTER
007F 00      406       ERRCNT  DB      0         ;COUNTING FOR TWO ERROR MODES
0080 00      407       DSPTST  DB      0         ;TEST FLAG
0081 00      408       COUNT4  DB      0         ;DROP COUNTER
0082 00      409       LSTRAT  DB      0         ;LAST RATE USED FOR ENCODED RATE KNOB
             410                  ;
0083 00      411       CKBEP   DB      0         ;CHECK BEEP FLAG USED IN CKCLR
0084 00      412       CKTIM   DB      0         ;USED IN CKCLR TO TIME BEEP
             413                  ;
             414
             415
     =1000   416               ORG     USRROM
             417       ;
             418       ;
             419       ;*****************************************************************
             420       ;                   CONSTANTS IN ROM
             421       ;*****************************************************************
             422       ;
1000 F8 9C FF 423      LO      DB      $F8,$9C,$FF       ;DISPLAY LO ON LEDS
1003 98 81 B8 424      BATT    DB      $98,$81,$B8       ;DISPLAY BAT ON LEDS
1006 B1 F8 C0 425      FLO     DB      $B1,$F8,$C0       ;DISPLAY FLO ON LEDS
1009 B0 BD BD 426      ERR     DB      $B0,$BD,$BD       ;DISPLAY ERR ON LEDS
100C 9D 9C FF 427      NO      DB      $9D,$9C,$FF       ;DISPLAY NO ON LEDS
100F 92 B0 B8 428      SET     DB      $92,$B0,$B8       ;DISPLAY SET ON LEDS
1012 89 F8 8C 429      HLD     DB      $89,$F8,$8C       ;DISPLAY HLD ON LEDS
1015 8C 9C 92 B0 430   DOSE    DB      $8C,$9C,$92,$B0   ;DISPLAY DOSE ON LEDS
1019 8C B0 F8 431      DEL     DB      $8C,$B0,$F8       ;DISPLAY OUT ON LEDS
101C 92 8A 92 432      SYS     DB      $92,$8A,$92       ;DISPLAY SYS ON LEDS
101F C0 CF A4 86 433   DIGITS  DB      $C0,$CF,$A4,$86,
1023 8B                        $8B       ;DISPLAY NUMBERS 0-9 ON LED
1024 92 90 C7 80 434           DB      $92,$90,$C7,$80,
1028 83                        $83
             435       ;
1029 F7 FB FD FE 436   DNUM    DB      $F7,$FB,$FD,$FE   ;DIGIT OUTPUT
             437       ;
             438       ;*****************************************************************
             439       ;
             440       $EJECT
             441       ;
             442       ;-----------------------------------------------------------------
             443       ;                   START FROM RESET
             444       ;-----------------------------------------------------------------
             445       ;
             446       ;         (THIS IS THE POWER-ON RESET ENTRY POINT)
             447       ;
             448       ;*****************************************************************
             449       ;
             450       ;
102D AE 40   451       RESET   LDX     #$40      ;FIRST, CLEAR RAM.
102F 4F      452               CLRA
1030 F7      453       CLEAR   STA     ,X
```

```
1031 5C            454            INCX
1032 A3 FF         455            CPX     #$FF
1034 26 FA         456            BNE     CLEAR
                   457
                   458    ;
                   459    ;            Set up the ports
                   460    ;
1036 CD 1106       461            JSR     TIMEON        ;GO START TIMER COUNTER
1039 1A 0A         462            BSET    5,MISC        ;SET INT SENSE FOR EDGE AND LEVEL
                   463    ;
                   464    ;            Wait for timer inturrupt
                   465    ;
103B 8F            466    LOOPW   WAIT
103C 20 FD         467            BRA     LOOPW
                   468    ;
                   469    $EJECT
                   470    ;
                   471    ;
                   472    ;
                   473    ;       -----------------------------------------------------------
                   474    ;                   EXTERNAL INTURRUPT HANDLER
                   475    ;       -----------------------------------------------------------
                   476    ;
                   477    ;
103E 1B 0A         478    ONPOW   BCLR    5,MISC        ;RETURN INT SENSE TO EDGE LEVEL
1040 0E 6E 45      479            BRSET   7,ERRON,NOON  ;IF IN ERROR MODE DONT DO
1043 04 6D 42      480            BRSET   2,PSTAT1,NOON ;DONT DO IF ON
                   481    ;
1046 A6 19         482            LDA     #$19          ;INITIALIZE PUMP STAT REGISTOR
1048 B7 6D         483            STA     PSTAT1
                   484    ;
                   485    ;       CHECK PORTB(6) FOR PUMP ID
                   486    ;
104A 1E 6D         487            BSET    7,PSTAT1      ;PRESET ID FLAG FOR 324
104C A6 FF         488            LDA     #$FF          ;PRELOAD ACCA TO SET PORTB ALL OUTPUT
104E 0D 01 04      489            BRCLR   6,PORTB,CONON ;IF PORTB(6)=0, PMP IS 324 SO CONTINUE
1051 1F 6D         490            BCLR    7,PSTAT1      ;ELSE, PMP IS 224 SO CLEAR ID FLAG
1053 A6 BF         491            LDA     #$BF          ; AND SET ACCA TO MAKE PORTB(6) INPUT
                   492    ;
1055 B7 05         493    CONON   STA     DDRB          ;CONFIGURE PORTB TO BF OR FF
1057 A6 FF         494            LDA     #$FF
1059 B7 04         495            STA     DDRA          ;CONFIGURE PORTA TO ALL OUTPUTS
105B B7 00         496            STA     PORTA         ;MAKE PORTA ALL 1'S
105D A6 1F         497            LDA     #$1F          ;
105F B7 01         498            STA     PORTB         ; PORTB=0001 1111
1061 A6 60         499            LDA     #$60          ;MAKE PORT D 0-4 INPUTS 5,6 OUTPUTS
1063 B7 07         500            STA     DDRD
1065 4F            501            CLRA
1066 B7 03         502            STA     PORTD
1068 B7 06         503            STA     DDRC
                   504    ;
                   505
                   506    ;            Initialize display pointers
                   507    ;
                   508                                  ;SET UP INITIAL DISPLAY
                   509                                  ;POINTERS SO DISPLAY
                   510                                  ;READS 0
                   511                                  ;WHEN THE DISPLAY IS
                   512                                  ;ACTIVATED
                   513    ;
106A 3F 79         514            CLR     VOLTIM        ;CLEAR THE VOLUME DISPLAY TIMER
                   515    ;
106C 5F            516            CLRX                  ;INITIALIZE DOSE
106D 4F            517            CLRA                  ;AND RATE
106E E7 51         518    CLEAR1  STA     DSPDG1,X      ;DISPLAY
1070 5C            519            INCX                  ;TO READ ZERO
1071 A3 07         520            CPX     #07           ;
1073 26 F9         521            BNE     CLEAR1        ;
1075 1A 74         522            BSET    5,ZEROST      ;SET DISPLAY ZERO FLAG
1077 14 71         523            BSET    2,DFLAG       ;SET DOSE ZERO FLAG
                   524    ;
1079 1D 6E         525            BCLR    6,VOLM        ;CLEAR THE VOLUME FLAG
107B 10 80         526            BSET    0,DSPTST      ;SET TEST FLAG
107D CD 1756       527            JSR     UPDATE        ;GO SET DISPLAY TO READ 125
1080 14 6D         528            BSET    2,PSTAT1      ;UNIT ON
                   529    ;
                   530    ;            INITIALIZE RATE KNOB LOCATION
                   531    ;
1082 B6 02         532            LDA     PORTC         ;GET PORTC
1084 A4 03         533            AND     #$03          ;MASK 2 LOWER BITS
1086 B7 82         534            STA     LSTRAT        ;STORE IN LAST RATE LOCATION
                   535    ;
1088 80            536    NOON    RTI
                   537    ;
                   538    ; \
                   539    $EJECT
```

```
                540    ;   ------------------------------------------------------------
                541    ;
                542    ;                    TIMER INTERRUPT ROUTINE
                543    ;   ------------------------------------------------------------
                544    ;
                545    ;         This routine is called every-
                546    ;
                547    ;   2.00 ms it services the LED mux.
                548    ;   8.00 ms it calls rpm, motor on, rate, hold, and off.
                549    ;   32.00 ms it checks  drop status and set.
                550    ;   .5000 s it checks for low battery, updates charge status and display on/off
                551    ;   142. s it checks charge time to control battery charge rate.
                552    ;
                553    ;   ************* 2  MS CHECK LOOP ********************************
                554    ;
1089 A6 F9      555    TIMINP  LDA     #$F9
108B B7 08      556            STA     TDR
108D 1F 09      557            BCLR    7,TCR              ;RESET THE TIMER
                558
                559    ;
108F CD 110C    560            JSR     WATCHD             ;GO OUTPUT PULSE TO HOLD OFF AUTO RESET
1092 CD 1115    561            JSR     LED                ;GO MULTIPLEX THE LEDS
1095 CD 12DA    562            JSR     INRATE1            ;GO UPDATE RATE FOR 224
1098 CD 1185    563            JSR     DROPCK             ;GO CHECK FOR DROP
                564    ;
109B B6 40      565            LDA     TS                 ;TEST IF TIME TO DO NEXT TESTS
109D 3C 40      566            INC     TS
109F A1 03      567            CMP     #T8MS
10A1 27 01      568            BEQ     TIME2
10A3 80         569            RTI
                570    ;
                571    ;   ************* 8 MS LOOP ***********************************
                572    ;
10A4 3F 40      573    TIME2   CLR     TS
                574    ;
10A6 CD 11CF    575            JSR     RPMCK              ;GO CHECK MOTOR FOR ONE RPM
10A9 CD 1290    576            JSR     MOTCK              ;GO CHECK MOTOR TIME TO TURN ON
10AC CD 12BD    577            JSR     SETCK              ;GO CHECK FOR SET CURRENT
10AF CD 140E    578            JSR     OFFCK              ;GO SEE IF OFF PUSHED
                579    ;
10B2 B6 41      580            LDA     T5                 ;GET STATUS OF SECOND TIMER
10B4 3C 41      581            INC     T5                 ;INCREMENT FOR NEXT TIME
10B6 A1 03      582            CMP     #T33MS             ;DOES IT EQUAL 32 MS
10B8 27 01      583            BEQ     TIME3              ;YES SO GO TEST
10BA 80         584            RTI                        ;RETURN TO PROGRAM
                585    ;
                586    ;   ************* 33 MSEC CHECK LOOP ******************************
                587    ;
10BB 3F 41      588    TIME3   CLR     T5                 ;CLEAR T5 FOR NEXT TIME THRU
                589    ;
10BD CD 1458    590            JSR     TESTD              ;DO TEST DISPLAY
10C0 CD 14EC    591            JSR     HOLDCK             ;GO TEST IF HOLD PRESSED
10C3 CD 15A9    592            JSR     DOSECK             ;GO CHECK DOSE BUTTON
10C6 CD 15EE    593            JSR     VOLDIS             ;DISPLAY VOLUME CHECK MODEL 324
10C9 CD 1640    594            JSR     CKCLR              ;GO CHECK VOLUME CLEAR
10CC CD 1687    595            JSR     INRATE2            ;INPUT ROUTINE FOR MODEL 324
                596    ;
10CF B6 42      597            LDA     T10                ;GET TIMER3 STATUS
10D1 3C 42      598            INC     T10                ;INCREMENT FOR NEXT TIME
10D3 A1 0F      599            CMP     #T1S               ;DOES IT EQUAL 1S
10D5 27 01      600            BEQ     TIME4              ;YES SO GO TIME4
10D7 80         601            RTI                        ;RETURN TO PROGRAM
                602    ;
                603    ;   ************* 1/2 SEC BAT CHECK ******************************
                604    ;
10D8 3F 42      605    TIME4   CLR     T10                ;RESET TIMER3 FOR NEXT TIME
                606    ;
10DA CD 17DD    607            JSR     ACDC               ;GO TEST AC OR DC
10DD CD 17E6    608            JSR     BATCK              ;GO DO BATTERY CHECK
10E0 CD 1836    609            JSR     DBATCK             ;GO CHECK FOR DEAD BATTERY
10E3 CD 184E    610            JSR     ALARM              ;GO TEST ALARM
10E6 CD 1860    611            JSR     BLINK              ;GO BLINK DISPLAY
10E9 CD 1909    612            JSR     HLDER              ;go test if on hold 142sec then error
                613    ;
10EC B6 43      614    NO5     LDA     T15                ;GET TIMER4 STATUS
10EE 3C 43      615            INC     T15                ;ADD ONE FOR NEXT TIME
10F0 A1 EF      616            CMP     #T142S             ;DOES IT EQUAL 142 SEC
10F2 27 01      617            BEQ     TIME5              ;YES SO GO TIME 5
10F4 80         618            RTI                        ;RETURN TO PROGRAM
                619    ;
                620    ;   ****************** 142 SEC LOOP *************************
                621    ;
```

```
10F5 3F 43              622        TIME5    CLR      T15              ;CLEAR FOR NEXT TIME
                        623        ;
                        624        ;
10F7 B6 44              625                 LDA      T20
10F9 3C 44              626                 INC      T20
10FB A1 02              627                 CMP      #T6M
10FD 27 01              628                 BEQ      TIME6
10FF 80                 629                 RTI
                        630        ;
                        631        ;     ******************* 2415 SEC LOOP *************************
                        632        ;
1100 3F 44              633        TIME6    CLR      T20
                        634        ;
1102 CD 192E            635                 JSR      TIM24            ;go test if off 24 hrs then kill power
                        636        ;
1105 80                 637                 RTI
                        638        ;
                        639        ;
                        640        $EJECT
                        641        ;===========================================================================
                        642        ;                                SUBROUTINES
                        643        ;===========================================================================
                        644        ;
                        645        ;
                        646        ;
                        647        ;                     INITIALIZE COUNTER TIMER
                        648        ;---------------------------------------------------------------------------
                        649        ;
                        650        ;
                        651        ;
1106 A6 02              652        TIMEON   LDA      #TIMEST          ;SET COUNTER TO 4
1108 B7 09              653                 STA      TCR              ;ENABLE TIMER INT
110A 9A                 654                 CLI                       ;ENABLE INTERRUPTS
110B 81                 655                 RTS                       ;RETURN;
                        656        ;
                        657        ;
                        658        ;
                        659        ;                     WATCH DOG TIMER
                        660        ;---------------------------------------------------------------------------
                        661        ;              Output clock to hold off reset
                        662        ;
110C 0B 03 03           663        WATCHD   BRCLR    5,PORTD,SETTR    ;IF CLOCK LOW MAKE HIGH
110F 1B 03              664                 BCLR     5,PORTD
1111 81                 665                 RTS
                        666        ;
1112 1A 03              667        SETTR    BSET     5,PORTD
1114 81                 668                 RTS
                        669        ;
                        670        $EJECT
                        671        ;.
                        672        ;
                        673        ;                     LED MUX ROUTINE
                        674        ;
                        675        ;       This routine is called every 4 ms
                        676        ;       It handles 0 supression and outputs 7 seg data
                        677        ;       VARIABLES USED: COUNT3=This is the digit number and is changed every
                        678        ;                             time this routine is called.
                        679        ;                      SAMPLE1=location of Current value of digit 1.
                        680        ;                              add count3 and use as pointer.
                        681        ;                      7,pstat2 (error)=test if in error mode for blinking.
                        682        ;                      4,pstat1 (display)=test if display blanked (blinking
                        683        ;                                mode).
                        684        ;                      ZEROST=bit 6 set=zero in msd
                        685        ;                             bit 7 set=zero in next digit
                        686        ;
                        687        ;
                        688        ;---------------------------------------------------------------------------
                        689        ;
1115 05 6D 36           690        LED      BRCLR    2,PSTAT1,NOD4    ;IF UNIT OFF DONT DO MUX
1118 A6 0F              691                 LDA      #$0F             ;Turn all digits off
111A BA 01              692                 ORA      PORTB
111C B7 01              693                 STA      PORTB
111E BE 64              694                 LDX      COUNT3           ;GET CURRENT DIGIT NO.
1120 A3 03              695                 CPX      #$03             ;HAVE WE DONE 4
1122 26 04              696                 BNE      GO               ;IF NOT GO ON
1124 3F 64              697                 CLR      COUNT3           ;IF SO RESET ALL VARIABLES
1126 20 02              698                 BRA      GO2
                        699        ;
1128 3C 64              700        GO       INC      COUNT3
                        701        ;
112A 0C 6E 0E           702        GO2      BRSET    6,VOLM,NOTZRO    ;IF IN VOL NO ZERO TEST
112D 00 71 0B           703                 BRSET    0,DFLAG,NOTZRO   ;IF IN DOSE NO ZERO TEST
1130 A3 03              704                 CPX      #$03             ;IF DIGIT 1 DONT TEST FOR 0
```

```
1132 27 07       705            BEQ     NOTZRO
1134 CD 1175     706            JSR     TEST0           ;GO TEST
1137 24 02       707            BCC     NOTZRO          ;IF NO CARRY IT CANT BE 0
1139 20 14       708            BRA     ZERO
                 709    ;
                 710    ;
113B E6 4D       711    NOTZRO  LDA     SAMPL1,X
113D 0E 6E 05    712            BRSET   7,ERRON,OUT1    ;IF error mode dont blank
1140 08 6D 02    713            BRSET   4,PSTAT1,OUT1   ;if display on flag set dont blank
1143 4F          714            CLRA                    ;blank display if display flag is low
1144 43          715            COMA                    ;SET PORTA=FF ALL OFF
                 716    ;
1145 B7 00       717    OUT1    STA     PORTA
1147 D6 1029     718            LDA     DNUM,X          ;GET DIGIT TO OUTPUT
114A B4 01       719            AND     PORTB           ;ENABLE
114C B7 01       720            STA     PORTA
114E 81          721    NOD4    RTS
                 722    ;
                 723    ;
114F A3 00       724    ZERO    CPX     #$00            ;IS THIS FIRST TIME THROUGH (MSD)
1151 27 17       725            BEQ     ZERO1           ;IF SO BLANK AND SET FLAG IF ZERO
1153 A3 01       726            CPX     #$01            ;IS THIS SECOND TIME THRU
1155 27 17       727            BEQ     ZERO2           ;IF SO CHECK FIRST FLAG
1157 0D 74 E1    728            BRCLR   6,ZEROST,NOTZRO ;ON THIRD TIME CHECK FIRST TWO
115A 0F 74 DE    729            BRCLR   7,ZEROST,NOTZRO ;IF EITHER NOT SET DONT BLANK
                 730    ;
115D E6 4D       731    ZEROT   LDA     SAMPL1,X        ;GET DIGIT DATA
115F 49          732            ROLA                    ;CHECK IF DP ON
1160 24 04       733            BCC     ZERODP          ;IF SO LEAVE ON
1162 A6 FF       734            LDA     #$FF            ;IF NOT BLANK
1164 20 DF       735            BRA     OUT1            ;GO OUTPUT IT
1166 A6 7F       736    ZERODP  LDA     #$7F            ;LEAVE DP ON
1168 20 DB       737            BRA     OUT1
                 738    ;
                 739    ;
116A 1C 74       740    ZERO1   BSET    6,ZEROST        ;SET ZERO FLAG
116C 20 EF       741            BRA     ZEROT           ;OUTPUT BLANK
116E 0D 74 CA    742    ZERO2   BRCLR   6,ZEROST,NOTZRO ;CHECK FIRST DIGIT FLAG
1171 1E 74       743            BSET    7,ZEROST        ;IF SET THEN BLANK 2ND DIGIT
1173 20 E8       744            BRA     ZEROT
                 745    ;
1175 E6 4D       746    TEST0   LDA     SAMPL1,X        ;test if digit is 0
1177 98          747            CLC
1178 49          748            ROLA
1179 A1 80       749            CMP     #$80
117B 27 04       750            BEQ     SETCAR
117D 98          751            CLC                     ;clr carry if not zero
117E E6 4D       752            LDA     SAMPL1,X
1180 81          753            RTS
1181 99          754    SETCAR  SEC                     ;set carry if it is
1182 E6 4D       755            LDA     SAMPL1,X
1184 81          756            RTS
                 757    ;
                 758    $EJECT
                 759    ;
                 760    ;             DROP CHECK
                 761    ;
                 762    ;       This routine is called every 8ms
                 763    ;       After a delay of .4 sec to clear all transients,
                 764    ;       it turns on the IR source and looks at the photo transistor.
                 765    ;       If the line is low a drop is there the counter is cleared.
                 766    ;       If there is no drop the counter is incremented and if it reaches
                 767    ;       a count of 95 or 95 X .008=.76 sec then the second counter is incremented
                 768    ;       This counter is tested in the RPM routine if it gets to 2 or 1.76s then
                 769    ;       it will alarm.
                 770    ;
                 771    ;-----------------------------------------------------------------
                 772    ;             Conditions
                 773    ;
1185 05 6D 43    774    DROPCK  BRCLR   2,PSTAT1,NODRP  ;DONT DO IF UNIT OFF
1188 00 6D 40    775            BRSET   0,PSTAT1,NODRP  ;DONT DO IF PUMP NOT IN RUN MODE
                 776    ;
                 777    ;       CHECK RATE
                 778    ;
118B B6 53       779            LDA     DSPDG3          ;IF RATE < 100, CHECK FOR DROPS
118D A1 01       780            CMP     #$01
118F 25 03       781            BLO     DELCK
1191 03 6D 37    782            BRCLR   1,PSTAT1,NODRP  ELSE, CHECK DROPS WHEN MOTOR ON ONLY
                 783    ;
                 784    ;       DELAY CHECK
                 785    ;
1194 B6 5B       786    DELCK   LDA     REG1            ;CHECK REG1
1196 A1 7C       787            CMP     #124            ;IF 0.248 SEC ELAPSED SINCE MOTOR ON
1198 27 04       788            BEQ     DROP1           ;DO DROP TEST AND SKIP INCREMENT.
```

```
119A 4C          789           INCA                        ;ELSE,
119B B7 5B       790           STA     REG1                ;INCREMENT AND RETURN.
119D 81          791           RTS
                 792     ;
                 793     ;        Test for drop
                 794     ;
119E 1C 03       795   DROP1   BSET    6,PORTD             ;TURN IR SOURCE ON
11A0 9D          796           NOP                         ;ADD SOME DELAY TO ALLOW SETTLING
11A1 9D          797           NOP
11A2 9D          798           NOP
11A3 9D          799           NOP
                 800     ;
11A4 0A 02 1C    801           BRSET   5,PORTC,CLERK       ;CHECK FOR LOW (DROP)
11A7 1D 03       802           BCLR    6,PORTD             ;TURN OFF IR SENSOR
11A9 10 81       803           BSET    0,COUNT4            ;WE HAVE DROP SO SET FLAG
                 804     ;
11AB 3C 5D       805           INC     DRCNT1              ;INCREMENT DROP COUNTERS
11AD 26 02       806           BNE     CONDRP
11AF 3C 5E       807           INC     DRCNT2
11B1 B6 5E       808   CONDRP  LDA     DRCNT2              ;CHECK IF DROP CNT = 0.76 SEC
11B3 A1 01       809           CMP     #$01
11B5 25 14       810           BLO     NODRP               ;IF DRCNT2 < 1 END TEST
11B7 B6 5D       811           LDA     DRCNT1              ;ELSE CHECK DROP CNT 1
11B9 A1 7C       812           CMP     #$7C
11BB 27 02       813           BEQ     NEXTBY              ;IF DRCNT1 >= 7C, INCREMENT REG3
11BD 20 0C       814           BRA     NODRP               ;ELSE, EXIT DROPCK
                 815     ;
11BF 3C 5F       816   NEXTBY  INC     REG3
11C1 20 08       817           BRA     NODRP               ;REG3 IS TESTED IN THE RPM ROUTINE
                 818     ;                                 ; IF 2 IT ERRORS
                 819     ;
                 820     ;       No drop
                 821     ;
11C3 1D 03       822   CLERK   BCLR    6,PORTD
11C5 3F 5D       823           CLR     DRCNT1              ;CLEAR THE COUNTERS FOR BLOCKED EYES
11C7 3F 5E       824           CLR     DRCNT2
11C9 3F 5F       825           CLR     REG3
11CB 81          826   NODRP   RTS
                 827     ;
                 828     ;
                 829     $EJECT
                 830     ;
                 831     ;
                 832     ;
                 833     ;                      RPM   CHECK
                 834     ;-------------------------------------------------------------
                 835     ;    This routine samples the hall effect line. At rates over 95 it stops
                 836     ;    the motor every 3 magnets or one rev. At rates under 100 it stops
                 837     ;    every magnet 1/3 rev.
11CC CC 1230     838   RPM3    JMP     RPM1
                 839     ;
                 840     ;       Conditions
                 841     ;
11CF 05 6D F9    842   RPMCK   BRCLR   2,PSTAT1,NODRP      ;DONT DO IF UNIT OFF
11D2 03 6D F6    843           BRCLR   1,PSTAT1,NODRP      ;DON'T DO IF MOTOR IS OFF
                 844     ;
                 845     ;       Delay until circuit settles
                 846     ;
11D5 B6 7E       847           LDA     MOTIM2              ;DON'T DO IF MOTOR NOT RUN ENOUGH
11D7 26 06       848           BNE     RPM2                ;IF 2ND BYTE >0 THEN DO TEST
11D9 B6 7D       849           LDA     MOTIM1              ;IF=0M THEN TEST 1ST BYTE FOR>$32
11DB A1 56       850           CMP     #86                 ;
11DD 25 EC       851           BLO     NODRP               ;IF <THEN 86*.00816=.7017 SEC THEN DONT DO
                 852     ;
                 853     ;       Test magnet
                 854     ;
11DF 00 03 EA    855   RPM2    BRSET   0,PORTD,RPM3        ;IF LINE HIGH THERE IS NO MAGNET
11E2 3F 7F       856           CLR     ERRCNT
11E4 3C 72       857           INC     LTEST               ;UPDATE MAG LOW COUNTER
11E6 B6 72       858           LDA     LTEST
11E8 A1 FF       859           CMP     #255                ;IF MAG SENSED FOR 2 CONS. SEC
11EA 27 62       860           BEQ     TIMERR              ;THEN MAGNET OR ROTOR ERROR.
11EC A1 01       861           CMP     #$01                ;IF LTEST > 1,
11EE 22 3F       862           BHI     NORPM               ;SAME PULSE DETECTED SO DON'T UPDATE
                 863     ;
                 864     ;--------- If this is model 324 add .376 to volume for every rev ---------
                 865     ;
11F0 0F 6D 12    866           BRCLR   7,PSTAT1,OFMOT1     ;IF 224 DONT ADD
                 867     ;
11F3 CD 126D     868           JSR     CALCV               ;ELSE, CALCULATE VOLUME
                 869     ;
                 870     ;
                 871     ;
11F6 0D 6E 06    872   XYZV    BRCLR   6,VOLM,OFMOT        ;IF NOT IN VOLUME MODE OR
```

```
11F9 00 75 03      873              BRSET   0,VFLAG,OFMOT    ;VOL TEST DISPLAY ENABLED
11FC CD 1634       874              JSR     VSEXP            ;GO UPDATE VOLUME NUMBERS
                   875       ;
                   876       ;----------------------------------------------------------------
                   877       ;
                   878       ;
                   879       ;     Test 1/3 OR 1 REV  AND Turn off the motor
                   880       ;
11FF B6 55         881      OFMOT   LDA     DS1              ;IF DOSE'=0, CHECK DOSE
1201 BA 56         882              ORA     DS2
1203 26 36         883              BNE     CMPDOS
                   884       ;
1205 3F 5B         885      OFMOT1  CLR     REG1
1207 3C 61         886              INC     REG5             ;CHECK IF THIS IS START UP
1209 B6 61         887              LDA     REG5             ;IF SO IGNORE THE FIRST MAGNET
120B A1 02         888              CMP     #$02             ;AS IT COULD BE LESS THEN 1/3
120D 25 20         889              BLO     NORPM            ;IT IS SO JUMP OVER SET CHECK
                   890       ;
120F 3A 61         891              DEC     REG5             ;ITS NOT START SO KEEP FROM OVERFLOW
1211 3C 7A         892              INC     THIRD1
1213 B6 7A         893              LDA     THIRD1
1215 A1 03         894              CMP     #$03
1217 26 0A         895              BNE     OFF90
1219 3F 7A         896              CLR     THIRD1
                   897       ;
                   898       ;     If drop flag not set then error
                   899       ;
121B 01 81 43      900              BRCLR   0,COUNT4,DROPER
121E 02 5F 40      901              BRSET   1,REG3,DROPER    ;EYES BLOCKED FOR 1 REV
                   902       ;
1221 3F 81         903              CLR     COUNT4
1223 B6 53         904      OFF90   LDA     DSPDG3           ;CHECK IF >95 RATE
1225 26 31         905              BNE     STP3             ;IF RATE >100 THEN STOP EVERY 3 SENSORS
1227 20 02         906              BRA     OFFM1
                   907       ;
1229 10 6D         908      OFFM    BSET    0,PSTAT1         ;SET HOLD FLAG TO DISABLE MOTCK
122B 13 6D         909      OFFM1   BCLR    1,PSTAT1         ;MOTOR OFF PSTAT
122D 1B 01         910              BCLR    5,PORTB          ;MOTOR OFF
122F 81            911      NORPM   RTS
                   912       ;
                   913       ;
                   914       ;
                   915       ;
                   916       ;
                   917       ;     Reset pulse status
                   918       ;
1230 3F 72         919      RPM1    CLR     LTEST            ;CLEAR MAG LOW COUNTER
1232 3C 7F         920              INC     ERRCNT
1234 B6 7F         921              LDA     ERRCNT
1236 A1 FF         922              CMP     #255             ;IF NO MAGNET IN 255X.008=2.04 SEC THEN ERR
1238 27 14         923              BEQ     TIMERR
123A 81            924              RTS
                   925       ;
                   926       ;
123B CD 1951       927      CMPDOS  JSR     CPVTOD           ;CALL COMPARE VOL TO DOSE
123E A3 FF         928              CPX     #$FF             ;X IS FF IF VOL >= DOSE
1240 26 C3         929              BNE     OFMOT1           ;IF X NOT FF, CONTINUE
                   930       ;                               ;ELSE DOSERR
                   931       ;
1242 10 70         932      DOSERR  BSET    0,DOSER
1244 B6 6E         933              LDA     PSTAT2
1246 AA A0         934              ORA     #$A0
1248 A4 BD         935              AND     #$BD
124A B7 6E         936              STA     PSTAT2
124C 20 DB         937              BRA     OFFM
                   938       ;
                   939       ;
124E 1E 6E         940      TIMERR  BSET    7,ERRON          ;ENABLE ERROR FLAG
1250 1A 6E         941              BSET    5,ALRM           ;ENABLE ALARM
1252 3F 7F         942              CLR     ERRCNT
1254 CD 1229       943              JSR     OFFM
1257 81            944              RTS
                   945       ;
                   946       ;     Count every 3 magnet hits
                   947       ;
1258 3C 7B         948      STP3    INC     THIRDR           ;BUMP THIRD OF A REV COUNTER;
125A B6 7B         949              LDA     THIRDR
125C A1 03         950              CMP     #$03             ;IF THIRD ONE THEN STOP
125E 24 CB         951              BHS     OFFM1            ;DONT SET HOLD FLAG
1260 81            952              RTS
                   953       ;
                   954       ;
                   955       ;     No drop error
                   956       ;
```

```
1261 14 6E    957     DROPER  BSET    2,NDROP         ;SET FLOW ERROR FLAG
1263 1E 6E    958             BSET    7,ERRON         ;ENABLE DISPLAY ERROR MODE
1265 1A 6E    959             BSET    5,ALRM          ;ENABLE ALARM ERROR
1267 1D 6E    960             BCLR    6,VOLM          ;GET OUT OF VOLUME MODE
1269 11 71    961             BCLR    0,DFLAG         ;CLEAR DOSE MODE FLAG
126B 20 BC    962             BRA     OFFM
              963     ;
              964     ;       •       .125 ml/ 1/3 rev 8*.125=1
              965     ;
126D 3C 58    966     CALCV   INC     DECML1          ;INCREMENT DECML COUNTER
126F B6 58    967             LDA     DECML1
1271 A1 08    968             CMP     #$08            ;IF DECML=8, TIME TO INCREMENT VS1, VS2
1273 26 1A    969             BNE     ENDCALC         ;ELSE, ENDCALC
              970     ;
1275 3F 58    971             CLR     DECML1          ;CLEAR DECML COUNTER
              972     ;
1277 A6 99    973             LDA     #$99            ;CHECK FOR FULL COUNTER
1279 B1 59    974             CMP     VS1
127B 26 04    975             BNE     CONCAL          ;IF VS1 != 99, CONTINUE CALCULATION
127D B1 5A    976             CMP     VS2             ;ELSE, CHECK VS2
127F 27 0E    977             BEQ     ENDCALC         ;IF VS1 & VS2 = 99, END CALCULATION
              978     ;
1281 B6 59    979     CONCAL  LDA     VS1             ;INCREMENT VS1
1283 AB 01    980             ADD     #$01
1285 8D       981             DAA                     ;DECIMAL ADJUST RESULT
1286 B7 59    982             STA     VS1             ;STORE VS1
              983     ;
1288 B6 5A    984             LDA     VS2             ;ADD VS2
128A A9 00    985             ADC     #$00
128C 8D       986             DAA                     ;DECIMAL ADHUST RESULT
128D B7 5A    987             STA     VS2             ;STORE RESULT
128F 81       988     ENDCALC RTS
              989     ;
              990     $EJECT
              991     ;
              992     ;                       TIMING THE MOTOR
              993     ;-----------------------------------------------------------------
              994     ;   This routine compares the calculated vs. timed motor on time and restarts
              995     ;       the motor every time they are equal.
              996     ;       The motor is turned off in the rpm routine)
              997     ;       the calculated values are generated by the UPDATE subroutine.
              998     ;
              999     ;       Variables: MOTIM1=INCREMENTED EACH TIME
              1000    ;                  MOTIM2=INCREMENTED EACH TIME MOTIM1 OVERFLOWS
              1001    ;                  TIMLO= CALCULATED FIRST BYTE OF TIME ON GENERATED IN UPDATE
              1002    ;                  TIMHI= CALCULATED SECOND BYTE OF TIME
              1003    ;
              1004    ;       Conditions
              1005    ;
1290 05 6D 29 1006    MOTCK   BRCLR   2,PSTAT1,END1   ;DONT DO IF UNIT OFF
1293 00 6D 26 1007            BRSET   0,PSTAT1,END1   ;DON'T DO IF HOLD
              1008    ;       BRSET   7,ERRON,END1    ;DON'T DO IF ERROR MODE
              1009            BRSET   3,PSTAT1,END1   ;DONT DO IF START MODE
              1010    ;
              1011    ;               ABOVE LINES DELETED TO ALLOW MOTOR TO
              1012    ;               PUMP WITH LO BAT ERROR
              1013    ;
              1014    ;
              1015    ;       Check if time running equals time calculated
              1016    ;
1296 98       1017            CLC
1297 B6 7D    1018            LDA     MOTIM1
1299 AB 01    1019            ADD     #$01
129B B7 7D    1020            STA     MOTIM1
129D 25 0D    1021            BCS     INCM2
129F B6 47    1022    BACK    LDA     TIMLO
12A1 B1 7D    1023            CMP     MOTIM1
12A3 26 17    1024            BNE     END1
12A5 B6 48    1025            LDA     TIMHI
12A7 B1 7E    1026            CMP     MOTIM2
12A9 27 07    1027            BEQ     MOTON
12AB 81       1028            RTS
              1029    ;
12AC 98       1030    INCM2   CLC
12AD 3C 7E    1031            INC     MOTIM2
12AF CC 129F  1032            JMP     BACK
              1033    ;
              1034    ;       Times are equal so turn motor on again
              1035    ;
12B2 12 6D    1036    MOTON   BSET    1,PSTAT1        ;MOTOR ON FLAG
12B4 1A 01    1037            BSET    5,PORTB         ;TURN MOTOR ON
12B6 3F 7B    1038            CLR     THIRDR          ;CLR    THIRD OF A REV COUNTER
12B8 3F 7D    1039            CLR     MOTIM1          ;RESET POINTER
12BA 3F 7E    1040            CLR     MOTIM2          ;
```

```
12BC 81            1041          END1    RTS
                   1042          ;
                   1043          ;
                   1044          $EJECT
                   1045          ;
                   1046          ;
                   1047          ;.                    SET CHECK
                   1048          ;-----------------------------------------------------------------
                   1049          ;       Conditions
                   1050          ;
12BD 05 6D 19      1051          SETCK   BRCLR   2,PSTAT1,NOSCK  ;DONT DO IF UNIT OFF
12C0 06 6D 16      1052                  BRSET   3,PSTAT1,NOSCK  ;DONT DO IF UNIT IS IN START MODE
12C3 00 6D 13      1053                  BRSET   0,PSTAT1,NOSCK  ;DONT DO IF UNIT IS IN HOLD
                   1054          ;
                   1055          ;       CHECK FOR PROPER SET PLACEMENT
                   1056          ;
12C6 07 02 10      1057                  BRCLR   3,PORTC,NOSCK   ;IF SET PRESENT, RETURN
                   1058          ;                                ;ELSE SET ERROR
12C9 18 6E         1059                  BSET    4,NOSET         ;ENABLE SET ERROR FLAG
12CB 1E 6E         1060                  BSET    7,ERRON         ;ENABLE ERROR MODE
12CD 1A 6E         1061                  BSET    5,ALRM          ;ENABLE AUDIO ALARM
12CF 1D 6E         1062                  BCLR    6,VOLM          ;GET OUT OF VOLUME MODE
12D1 11 71         1063                  BCLR    0,DFLAG         ;CLEAR DOSE MODE FLAG
12D3 13 6D         1064                  BCLR    1,PSTAT1        ;CLEAR MOTOR ON FLAG
12D5 1B 01         1065                  BCLR    5,PORTB         ;TURN OFF MOTOR
12D7 10 6D         1066                  BSET    0,PSTAT1        ;SET HOLD FLAG TO DISABLE MOTCK
                   1067          ;
12D9 81            1068          NOSCK   RTS
                   1069
                   1070
                   1071
                   1072
                   1073          $EJECT
                   1074          ;
                   1075          ;
                   1076          ;                 INPUTING THE RATE (model 224)
                   1077          ;-----------------------------------------------------------------
                   1078          ;       Conditions
                   1079          ;
12DA 05 6D 40      1080          INRATE1 BRCLR   2,PSTAT1,OVER   ;DONT DO IF OFF
12DD 00 80 3D      1081                  BRSET   0,DSPTST,OVER   ;DONT DO IF TEST MODE
12E0 00 6E 3A      1082                  BRSET   0,LOWBAT,OVER   ;DONT DO IF LOWBAT
12E3 0E 6E 37      1083                  BRSET   7,ERRON,OVER    ;DONT DO IF ERROR MODE
12E6 0E 6D 34      1084                  BRSET   7,PSTAT1,OVER   ;DONT DO IF MODEL 324
12E9 06 6D 03      1085                  BRSET   3,PSTAT1,CKRTE  ;IF START MODE DO
12EC 01 6D 2E      1086                  BRCLR   0,PSTAT1,OVER   ;DONT DO IN HOLD OFF MODE
                   1087          ;
                   1088          ;       DECODE RATE SWITCH
                   1089          ;
12EF 38 82         1090          CKRTE   LSL     LSTRAT          ;SHIFT LSTRAT LEFT 2 BITS
12F1 38 82         1091                  LSL     LSTRAT
12F3 B6 02         1092                  LDA     PORTC           ;GET AND MASK CURRENT KNOB POSITION
12F5 A4 03         1093                  AND     #$03
12F7 BA 82         1094                  ORA     LSTRAT          ;MERGE PREVIOUS AND CURRENT POSITIONS
12F9 A4 0F         1095                  AND     #$0F            ;MASK OUT UPPER NIBBLE
12FB B7 82         1096                  STA     LSTRAT          ;STORE RATE POSITION FOR NEXT TIME
                   1097          ;
12FD A1 01         1098                  CMP     #$01            ;BEGIN DECODING DEC POSITIONS
12FF 27 64         1099                  BEQ     DECR1
1301 A1 07         1100                  CMP     #$07
1303 27 60         1101                  BEQ     DECR1
1305 A1 08         1102                  CMP     #$08
1307 27 5C         1103                  BEQ     DECR1
1309 A1 0E         1104                  CMP     #$0E
130B 27 5A         1105                  BEQ     DECR1
                   1106          ;
130D A1 02         1107                  CMP     #$02            ;BEGIN DECODING INC POSITIONS
130F 27 0D         1108                  BEQ     INCR1
1311 A1 04         1109                  CMP     #$04
1313 27 09         1110                  BEQ     INCR1
1315 A1 0B         1111                  CMP     #$0B
1317 27 05         1112                  BEQ     INCR1
1319 A1 0D         1113                  CMP     #$0D
131B 27 01         1114                  BEQ     INCR1
131D 81            1115          OVER    RTS
                   1116
                   1117          ;         test for increase by one
                   1118          ;
131E 1B 74         1119          INCR1   BCLR    5,ZEROST        ;CLEAR DISPLAY ZERO FLAG
1320 16 6D         1120                  BSET    3,PSTAT1        ;MAKE START ON
1322 18 6D         1121                  BSET    4,PSTAT1        ;MAKE DISPLAY ON
1324 A6 03         1122                  LDA     #$03            ;IF 300, RETURN
1326 B1 53         1123                  CMP     DSPDG3
1328 27 F3         1124                  BEQ     OVER
                   1125          ;
132A 0F 6D 1A      1126                  BRCLR   7,PSTAT1,UPFIVE ;IF MODEL 224 GO UP BY 5 ONLY
```

```
                1127    ;
                1128    ;                               ;IF RATE )= 50, INCREMENT BY 5
132D B6 53      1129            LDA     DSPDG3          ;
132F 26 16      1130            BNE     UPFIVE          ;IF DIGIT 3 IS NOT 0, INCREMENT BY 5
1331 B6 52      1131            LDA     DSPDG2
1333 A1 05      1132            CMP     #$05
1335 24 10      1133            BHS     UPFIVE          ;IF DIGIT 2 IS )= 5, INCREMENT BY 5
                1134    ;
1337 98         1135    UPONE   CLC                     ;ELSE INCREMENT BY 1
1338 A6 F7      1136            LDA     #$F7            ;TEST FOR 9
133A BB 51      1137            ADD     DSPDG1
133C 25 05      1138            BCS     DEC91           ;IF 9 MAKE 0 AND INC NEXT DIGIT
133E 3C 51      1139            INC     DSPDG1          ;IF NOT THEN INC BY ONE
1340 CC 1756    1140            JMP     UPDATE
                1141    ;
1343 3F 51      1142    DEC91   CLR     DSPDG1
1345 20 09      1143            BRA     INC2
                1144    ;
                1145    ;       increment by five
                1146    ;
                1147    ;
1347 CD 174B    1148    UPFIVE  JSR     TOGGLE          ;ELSE INCR BY 5
134A A6 05      1149            LDA     #$05
134C B1 51      1150            CMP     DSPDG1
134E 27 12      1151            BEQ     DEC3
                1152    ;
                1153    ;       Increment digit 2 by one
                1154    ;
1350 98         1155    INC2    CLC                     ;IF DIGITB IS 9 THEN GO MAKE IT 0
1351 A6 F7      1156            LDA     #$F7            ;ADD 255-8 TO DIGITB
1353 BB 52      1157            ADD     DSPDG2          ;IF OVER FLOW THEN MAKE 0
1355 25 05      1158            BCS     DEC9
1357 3C 52      1159            INC     DSPDG2          ;IF OK THEN DIGIT=DIGIT+1
1359 CC 1756    1160            JMP     UPDATE          ;NOW GO DO DIGIT3
135C 3F 52      1161    DEC9    CLR     DSPDG2          ;DIGIT2=0
                1162    ;
                1163    ;       Increment digit 3 by one
                1164    ;
135E 3C 53      1165    INC3    INC     DSPDG3
1360 1F 74      1166            BCLR    7,ZEROST
1362 CC 1756    1167    DEC3    JMP     UPDATE
                1168    ;
                1169    ;       Do a rate decrease
                1170    ;
                1171    ;       test for decrement by 5
                1172    ;
1365 16 6D      1173    DECR1   BSET    3,PSTAT1        ;MAKE START ON
1367 18 6D      1174            BSET    4,PSTAT1        ;MAKE DISPLAY ON
1369 0A 74 B1   1175            BRSET   5,ZEROST,OVER   ;IF DISPLAY IS 0 THEN DONT DECR
136C B6 53      1176            LDA     DSPDG3          ;PREPARE ACCA FOR ZERO TEST OF
136E BA 52      1177            ORA     DSPDG2          ;DSPDG2 AND DSPDG3
1370 0E 6D 03   1178            BRSET   7,PSTAT1,CH324  ;IF 324 GOTO CH324, ELSE
1373 26 62      1179    CH224   BNE     DECR5           ;IF 224 AND DIGIT 2 & 3 ARE NOT ZERO, DECR5
1375 81         1180            RTS                     ;ELSE DONT DECR
                1181    ;
1376 26 07      1182    CH324   BNE     DECCN           ;IF DIGIT2 & 3 ARE NOT ZERO, CONTINUE
1378 B6 51      1183            LDA     DSPDG1          ;ELSE, TEST DIGIT 1 FOR 1
137A A1 01      1184            CMP     #$01
137C 26 13      1185            BNE     DOWN1           ;IF NOT 1,DECR BY 1
137E 81         1186            RTS
                1187    ;
137F B6 53      1188    DECCN   LDA     DSPDG3          ;IF DIGIT3 NOT ZERO,
1381 26 54      1189            BNE     DECR5           ;DECR BY 5
1383 B6 52      1190            LDA     DSPDG2          ;IF DIGIT2 ) 5,
1385 A1 05      1191            CMP     #$05            ;
1387 22 4E      1192            BHI     DECR5           ;DECR BY 5
1389 25 06      1193            BLO     DOWN1           ;ELSEIF DIGIT2 ( 5 DECR BY 1
138B B6 51      1194            LDA     DSPDG1          ;ELSE TEST DIGIT1
138D A1 00      1195            CMP     #$00            ;IF DIGIT1 NOT ZERO,
138F 26 46      1196            BNE     DECR5           ;DECR BY 5
                1197
                1198    ;
                1199    ;       DECREMENT BY 1
                1200    ;
1391 B6 51      1201    DOWN1   LDA     DSPDG1          ;GET DIGIT 1
1393 27 09      1202            BEQ     TET2            ;IF ZERO THEN MAKE 9
1395 A1 01      1203            CMP     #$01
1397 27 34      1204            BEQ     CHK300
1399 3A 51      1205    DEC2    DEC     DSPDG1          ;IF NOT THEN JUST DECREMENT
139B CC 1756    1206            JMP     UPDATE          ;GO UPDATE THE RATE
                1207    ;
139E B6 52      1208    TET2    LDA     DSPDG2
13A0 26 0B      1209            BNE     INC9A
13A2 3A 53      1210            DEC     DSPDG3
```

```
13A4 A6 09      1211            LDA     #$09
13A6 B7 51      1212            STA     DSPDG1
13A8 B7 52      1213            STA     DSPDG2
13AA CC 1756    1214            JMP     UPDATE
                1215    ;
13AD 3A 52      1216    INC9A   DEC     DSPDG2          ;IF NOT DECREMENT BY ONE
13AF A6 09      1217            LDA     #$09            ;MAKE FIRST DIGIT 9
13B1 B7 51      1218            STA     DSPDG1
13B3 CC 1756    1219            JMP     UPDATE          ;GO UPDATE THE DISPLAY
                1220    ;
13B6 A6 03      1221    GO300   LDA     #$03            ;CHANGE DIGIT 3 TO 3
13B8 B7 53      1222            STA     DSPDG3
13BA A6 00      1223            LDA     #$00            ;MAKE DISPLAY 300
13BC B7 52      1224            STA     DSPDG2
13BE B7 51      1225            STA     DSPDG1
                1226    ;       CLR     ZEROST
13C0 B6 78      1227            LDA     SPEED1
13C2 A1 40      1228            CMP     #$40
13C4 25 04      1229            BLO     SPDY1
13C6 A6 41      1230            LDA     #$41
13C8 B7 78      1231            STA     SPEED1
13CA CC 1756    1232    SPDY1   JMP     UPDATE
                1233    ;
13CD B6 52      1234    CHK300  LDA     DSPDG2          ;IF DIGIT 2 IS ZERO MAKE 300
13CF 26 C8      1235            BNE     DEC2
13D1 B6 53      1236            LDA     DSPDG3
13D3 26 C4      1237            BNE     DEC2
13D5 20 DF      1238            BRA     GO300
                1239    ;
                1240    ;       change rate by 5
                1241    ;
13D7 4F         1242    DECR5   CLRA
13D8 B1 53      1243            CMP     DSPDG3          ;IF DIGIT 2,3 ARE 0 THEN MAKE 000
13DA 26 0D      1244            BNE     TOG2
13DC B1 52      1245            CMP     DSPDG2
13DE 26 09      1246            BNE     TOG2
13E0 B7 51      1247            STA     DSPDG1
13E2 A6 03      1248            LDA     #$03
13E4 B7 53      1249            STA     DSPDG3
                1250    ;       CLR     ZEROST
13E6 CC 1756    1251            JMP     UPDATE
13E9 CD 1748    1252    TOG2    JSR     TOGGLE          ;GO MAKE 0 OR 5
13EC A6 00      1253            LDA     #$00
13EE B1 51      1254            CMP     DSPDG1
13F0 27 19      1255            BEQ     INCD3
                1256    ;
                1257    ;       Decrement digit 2 by one
                1258    ;
13F2 B6 52      1259            LDA     DSPDG2          ;GET POINTER
13F4 27 05      1260            BEQ     INC9            ;IF 0 THEN MAKE 9
13F6 3A 52      1261            DEC     DSPDG2          ;IF)0 THEN SUB 1
13F8 CC 1756    1262    SETZ    JMP     UPDATE          ;GO DO DIGIT 3
13FB B6 53      1263    INC9    LDA     DSPDG3
13FD 27 0C      1264            BEQ     INCD3
13FF A6 09      1265            LDA     #$09            ;RESET TO 9
1401 B7 52      1266            STA     DSPDG2
                1267    ;
                1268    ;       Decrement digit 3 by one
                1269    ;
1403 B6 53      1270    DECD3   LDA     DSPDG3          ;GET DIGIT 3 POINTER
1405 27 04      1271            BEQ     INCD3           ;IF 0 THEN MAKE 2
1407 3A 53      1272            DEC     DSPDG3          ;)0 SO SUB 1
1409 1F 74      1273            BCLR    7,ZEROST
140B CC 1756    1274    INCD3   JMP     UPDATE
                1275    ;
                1276    ;
                1277    $EJECT
                1278    ;
                1279    ;
                1280    ;                       OFF CHECK
                1281    ;---------------------------------------------------------------
                1282    ;       Conditions
                1283    ;
140E 05 6D 2C   1284    OFFCK   BRCLR   2,PSTAT1,TSTCK  ;IF OFF, CHECK IF TIME FOR TEST MODE
1411 05 02 01   1285            BRCLR   2,PORTC,GOFF    ;IF OFF BUTTON PRESSED GO OFF
1414 81         1286    NOOFF   RTS
                1287    ;
                1288    ;       Do off
                1289    ;
1415 00 6E 1E   1290    GOFF    BRSET   0,LOWBAT,KILLP1 ;IF LOW BATT KILL POWER
1418 3F 6E      1291            CLR     PSTAT2          ;NO ALARMS OR OPTIONAL MODES
141A 3F 71      1292            CLR     DFLAG           ;CLEAR DOSE FLAG
141C 3F 80      1293            CLR     DSPTST          ;CLEAR DISPLAY TEST FLAG
                1294    ;
```

```
141E A6 19      1295            LDA     #$19            ;SET PSTAT1 FOR NEXT TURN-ON
1420 B7 6D      1296            STA     PSTAT1
1422 A6 1F      1297            LDA     #$1F            ;KILL DISPLAY AND MOTOR  0001 1111 OR
1424 B7 01      1298            STA     PORTB
1426 CD 1948    1299            JSR     TIMRST          ;CLEAR ALL TIMERS FOR 24HR KEEPING
1429 3F 45      1300            CLR     T25
142B 3F 55      1301            CLR     DS1             ;CLEAR DS1 AND DS2 FOR USE AS
142D 3F 56      1302            CLR     DS2             ;3 SEC TEST TIMER.
142F 8F         1303    LOOPF   WAIT                    ; GO SLEEP
1430 20 FD      1304            BRA     LOOPF
                1305    ;
                1306    ;       wake up by on button (external int)
                1307    ;
1432 CD 1196    1308            JSR     TIMEON          ;RESET COUNTER TIMER
1435 81         1309            RTS
                1310    ;
1436 9B         1311    KILLP1  SEI                     ;SET INT MASK TO PREVENT TURN-ON
1437 A6 0F      1312            LDA     #$0F            ;DISABLE PUMP
1439 B7 01      1313            STA     PORTB
143B 20 F9      1314            BRA     KILLP1          ;LOOP UNTILL POWER DISSIPATES
                1315    ;
                1316    ;       TEST CHECK
                1317    ;
143D 04 02 03   1318    TSTCK   BRSET   2,PORTC,TSTOUT  ;IF OFF BUTTON NOT PUSHED, RETURN
1440 05 03 05   1319            BRCLR   2,PORTD,TSTCNT  ;ELSE, IF HOLD BUTTON PRESSED INCREMENT
                1320    ;                               ; TES COUNTER
1443 3F 55      1321    TSTOUT  CLR     DS1
1445 3F 56      1322            CLR     DS2
1447 81         1323            RTS
                1324    ;
1448 3C 55      1325    TSTCNT  INC     DS1             ;INCREMENT TEST TIMER
144A 26 02      1326            BNE     TST1
144C 3C 56      1327            INC     DS2
144E B6 56      1328    TST1    LDA     DS2             ;IF 3 SEC ELAPSED, GOTO PMPTST
1450 A1 02      1329            CMP     #$02
1452 24 01      1330            BHS     PTST
1454 81         1331            RTS                     ;ELSE RETURN
1455 CC 1C00    1332    PTST    JMP     PMPTST
                1333    ;
                1334    $EJECT
                1335    ;
                1336
                1337    ;               TEST MODE
                1338    ;-----------------------------------------------------------------------
                1339    ;
1458 05 6D 30   1340    TESTD   BRCLR   2,PSTAT1,NOTST  ;DONT DO IF UNIT OFF
145B 01 80 2D   1341            BRCLR   0,DSPTST,NOTST  ;DONT DO IF TEST FLAG NOT SET
145E 0F 6D 2D   1342            BRCLR   7,PSTAT1,TSTD2  ;IF 224, DO SHORT TEST MODE
1461 3C 79      1343            INC     VOLTIM          ;DO FOR .033*60=1.98 SEC
1463 B6 79      1344            LDA     VOLTIM
1465 A1 78      1345            CMP     #120            ;GO CLEAR TEST MODE
1467 22 4F      1346            BHI     CLTEST
1469 A1 64      1347            CMP     #100            ;GO DISPLAY DOSE NUMBER
146B 22 7B      1348            BHI     DOSDIS
146D A1 50      1349            CMP     #80             ;GO DISPLAY DOSE
146F 22 66      1350            BHI     DOSTST
1471 A1 3C      1351            CMP     #60             ;GO DISPLAY VOLUME NUMBER
1473 22 5E      1352            BHI     VOLDS
1475 A1 28      1353            CMP     #40             ;GO DISPLAY VOL
1477 22 49      1354            BHI     VOLTST
1479 A1 14      1355            CMP     #20             ;GO KILL ALARM FIRST
147B 22 22      1356            BHI     CLATST
147D 1E 01      1357    CONTST  BSET    7,PORTB         ;ALARM ON
147F 1C 01      1358            BSET    6,PORTB         ;CLEAR LED ON
1481 1C 6E      1359            BSET    6,VOLM          ;SET VOLM FLAG TO ENABL 4 DIGITS
1483 3F 4D      1360            CLR     SAMPL1          ;MAKE DISPLAY "8888"
1485 3F 4E      1361            CLR     SAMPL2
1487 3F 4F      1362            CLR     SAMPL3
1489 3F 50      1363            CLR     SAMPL4
148B 1D 03      1364    NOTST   BCLR    6,PORTD         ;TURN IR SOURCE OFF
148D 81         1365            RTS
                1366    ;
                1367    ;       SHORT TEST FOR K224
                1368    ;
148E 1C 6E      1369    TSTD2   BSET    6,PSTAT2        ;VOLUME FLAG SET TO ENABLE 4 DIGITS
1490 3C 79      1370            INC     VOLTIM          ;DO FOR .033*60=1.98 SEC
1492 B6 79      1371            LDA     VOLTIM
1494 A1 3C      1372            CMP     #$3C
1496 22 20      1373            BHI     CLTEST
1498 A1 14      1374            CMP     #$14
149A 22 03      1375            BHI     CLATST
149C CC 147D    1376            JMP     CONTST
                1377    ;
                1378
```

```
149F 1F 01      1379    CLATST  BCLR    7,PORTB         ;TURN ALARM OFF
14A1 1D 01      1380            BCLR    6,PORTB         ;LED OFF
                1381    ;
                1382    ;       test sensor eyes
                1383    ;
14A3 1C 03      1384            BSET    6,PORTD         ;TURN IR SOURCE ON
14A5 9D         1385            NOP                     ;ADD 8 USEC DELAY TO ALLOW IR
14A6 9D         1386            NOP                     ;SENSOR TO SETTLE
14A7 9D         1387            NOP
14A8 9D         1388            NOP
14A9 0A 02 DF   1389            BRSET   5,PORTC,NOTST   ;IF RECIEVER LOW EYES BLOCKED THEN ERROR
14AC 1D 03      1390            BCLR    6,PORTD         ;TURN OFF IR SOURCE
14AE 1A 6E      1391            BSET    5,PSTAT2        ;ENABLE ALARM
14B0 14 6E      1392            BSET    2,NDROP         ;ENABLE FLOW ERROR FLAG
14B2 1E 6E      1393            BSET    7,PSTAT2        ;ENABLE ERROR FLAG
14B4 1F 01      1394            BCLR    7,PORTB         ;TURN ALARM OFF
14B6 17 6D      1395            BCLR    3,PSTAT1        ;CLEAR START FLAG
                1396    ;
14B8 CD 1756    1397    CLTEST  JSR     UPDATE          ;RESTORE DISPLAY
14BB 3F 80      1398            CLR     DSPTST          ;CLEAR TEST FLAG
14BD 1D 6E      1399            BCLR    6,VOLM          ;CLEAR VOLUME FLAG FOR 224
14BF 3F 79      1400            CLR     VOLTIM          ;CLEAR TIMER
14C1 81         1401            RTS
                1402    ;
14C2 A6 F8      1403    VOLTST  LDA     #$F8            ;
14C4 B7 50      1404            STA     SAMPL4
14C6 A6 9C      1405            LDA     #$9C
14C8 B7 4F      1406            STA     SAMPL3
14CA A6 C8      1407            LDA     #$C8
14CC B7 4E      1408            STA     SAMPL2
14CE A6 FF      1409            LDA     #$FF
14D0 B7 4D      1410            STA     SAMPL1
14D2 81         1411            RTS
                1412    ;
14D3 CD 1634    1413    VOLDS   JSR     VSEXP
14D6 81         1414            RTS
                1415    ;
14D7 A6 B0      1416    DOSTST  LDA     #$B0
14D9 B7 50      1417            STA     SAMPL4
14DB A6 92      1418            LDA     #$92
14DD B7 4F      1419            STA     SAMPL3
14DF A6 9C      1420            LDA     #$9C
14E1 B7 4E      1421            STA     SAMPL2
14E3 A6 8C      1422            LDA     #$8C
14E5 B7 4D      1423            STA     SAMPL1
14E7 81         1424            RTS
                1425    ;
14E8 CD 1745    1426    DOSDIS  JSR     DSEXP           ;DISPLAY PROGRAMMED DOSE
14EB 81         1427            RTS
                1428
                1429
                1430    ;
                1431    $EJECT
                1432    ;
                1433    ;                HOLD CHECK
                1434    ;-----------------------------------------------------------------
                1435    ;       Conditions
                1436    ;
14EC 05 6D 43   1437    HOLDCK  BRCLR   2,PSTAT1,NOHOLD ;IF OFF DONT DO
14EF 00 80 40   1438            BRSET   0,DSPTST,NOHOLD ;DONT DO IF TEST MODE
14F2 00 76 3D   1439            BRSET   0,CWF,NOHOLD    ;DONT DO IF INC OR DEC
14F5 00 77 3A   1440            BRSET   0,CCWF,NOHOLD   ;BUTTON IS PRESSED
                1441    ;
14F8 04 03 38   1442            BRSET   2,PORTD,NOH1    ;IS HOLD BUTTON DOWN RETURN IF NOT
                1443    ;
                1444    ;       Hold  button down
                1445    ;
                1446    ;       Debounce switch
                1447    ;
14FB 00 73 34   1448            BRSET   0,HTEST,NOHOLD  ;WE MUST BE SEEING SAME PULSE SO IGNORE
14FE 10 73      1449            BSET    0,HTEST         ;IF NOT SAME SET THE FLAG
                1450    ;
                1451    ;       CLEAR HOLD TIME COUNTERS
                1452    ;
1500 3F 4B      1453            CLR     HLDTM1
1502 3F 4C      1454            CLR     HLDTM2
                1455    ;
                1456    ;       Check for alarm conditions
                1457    ;
1504 00 6E 2F   1458            BRSET   0,LOWBAT,HLDBAT ;IF LOW BAT,STOP ALARM AND MOTOR.
1507 00 70 37   1459            BRSET   0,DOSER,STDOSE  ;IF DOSE DEL FLAG SET, STOP DOSE MESS.
```

```
150A 0A 6E 2F   1460           BRSET   5,ALRM,NOAUDO   ;IF WE ARE ALARMING THEN KILL AUDIO
150D 0F 6E 3F   1461           BRSET   7,ERRON,NOMESS  ;IF WE ARE FLASHING ERROR MESSAGE THEN GO RUN
1510 0C 6E 34   1462           BRSET   6,VOLM,NOVOLM   ;IF IN VOL GO RESTORE RATE
1513 00 71 35   1463           BRSET   0,DFLAG,NODOS   ;IF DOSE MODE, GO RESTORE RATE
                1464   ;
                1465   ;              Are we in hold now run if yes, hold if not
1516 06 6D 3E   1466           BRSET   3,PSTAT1,RUN    ;IF IN START MODE THEN DO RUN
                1467   ;
1519 00 6D 3B   1468           BRSET   0,PSTAT1,RUN    ;IF YES GO RUN
151C 10 6D      1469   HOLD    BSET    0,PSTAT1        ;IF NOT SET HOLD FLAG
151E 1B 01      1470           BCLR    5,PORTB         ;MOTOR OFF
1520 13 6D      1471           BCLR    1,PSTAT1        ;CLEAR MOTOR ON FLAG
                1472   ;
1522 B6 02      1473           LDA     PORTC           ;RE-INITIALIZE RATE KNOB
1524 A4 03      1474           AND     #$03
1526 B7 82      1475           STA     LSTRAT
                1476   ;
1528 3F 6E      1477           CLR     PSTAT2
152A 3F 70      1478           CLR     DOSER           ;CLR DOSE ERROR FLAG
152C CD 1756    1479           JSR     UPDATE          ;RESTORE DIGITS TO KILL SCROLLING DP
152F CD 1948    1480           JSR     TIMRST
1532 81         1481   NOHOLD  RTS
                1482   ;
                1483   ;          Hold button not down so reset the flag and return
                1484   ;
1533 11 73      1485   NOH1    BCLR    0,HTEST
1535 81         1486           RTS
                1487   ;
                1488   ;              LOW BAT HOLD
                1489   ;
                1490   ;              kill motor
                1491   ;
1536 13 6D      1492   HLDBAT  BCLR    1,PSTAT1        ;CLEAR MOTOR ON FLAG
1538 1B 01      1493           BCLR    5,PORTB         ;TURN MOTOR OFF
153A 10 6D      1494           BSET    0,PSTAT1        ;SET HOLD FLAG
                1495   ;
                1496   ;              AND
                1497   ;
                1498   ;              Kill the audio
                1499   ;
153C 1B 6E      1500   NOAUDO  BCLR    5,ALRM          ;RESET BEEPER FLAG
153E 1F 01      1501           BCLR    7,PORTB         ;STOP AUDIO NOW
1540 81         1502           RTS
                1503   ;
                1504   ;              STOP DOSE DELIVIRED MESSAGE
                1505   ;
1541 1D 6E      1506   STDOSE  BCLR    6,VOLM          ;CLEAR ALARM FLAG
1543 1F 01      1507           BCLR    7,PORTB         ;STOP ALARM
1545 20 D5      1508           BRA     HOLD            ;PUT PUMP IN HOLD
                1509   ;
                1510   ;          Recovery from error KILL THE MESSAGE
                1511   ;
1547 1D 6E      1512   NOVOLM  BCLR    6,VOLM
1549 20 D1      1513           BRA     HOLD
                1514   ;
154B 11 71      1515   NODOS   BCLR    0,DFLAG
154D 20 CD      1516           BRA     HOLD
                1517   ;
                1518   ;
154F 3F 6E      1519   NOMESS  CLR     PSTAT2
1551 CD 1756    1520           JSR     UPDATE          ;RESTORE DISPLAY TO RATE
1554 CC 1557    1521           JMP     RUN             ;GO RUN MOTOR
                1522   ;
                1523   ;
                1524   ;
                1525   ;---------------------- RUN MOTOR PUMPING ----------------------
                1526   ;
                1527   ;
1557 17 6D      1528   RUN     BCLR    3,PSTAT1        ;SET UNIT START OFF
1559 18 6D      1529           BSET    4,PSTAT1        ;SET DISPLAY ON
                1530   ;
155B B6 55      1531           LDA     DS1             ;CHECK IF DOSE DEL BEFORE TURNING
155D BA 56      1532           ORA     DS2             ;MOTOR ON
155F 27 16      1533           BEQ     RUN1            ;IF DOSE = 0, NO NEED TO CHECK
1561 CD 1951    1534           JSR     CPVTOD          ;ELSE, CALL CMP VOL TO DOSE ROUTINE
1564 A3 FF      1535           CPX     #$FF            ;X IS FF IF VOL )= DOSE
1566 26 0F      1536           BNE     RUN1            ;IF X '= FF, OK TO START MOTOR
                1537   ;
```

```
1568 10 70    1538            BSET    0,DOSER        ;ELSE, SET DOSE DEL MESSAGE
156A 10 6D    1539            BSET    0,PSTAT1       ;SET HOLD FLAG TO DISABLE MOTCK
156C 1E 6E    1540            BSET    7,ERRON        ;ENABLE ERROR FLAG
156E 1A 6E    1541            BSET    5,ALRM         ;ENABLE ALARM
1570 1D 6E    1542            BCLR    6,VOLM         ;CLEAR VOL MODE FLAG
1572 11 71    1543            BCLR    0,DFLAG        ;CLEAR DOSE MODE FLAG
1574 19 6E    1544            BCLR    4,NOSET        ;CLR NO SET FLAG
1576 81       1545            RTS
              1546    ;
              1547    ;
1577 3F 7D    1548    RUN1    CLR     MOTIM1
1579 3F 7E    1549            CLR     MOTIM2
157B 3F 81    1550            CLR     COUNT4
157D 3F 63    1551            CLR     COUNT2
157F 3F 5B    1552            CLR     REG1
1581 3F 5D    1553            CLR     DRCNT1
1583 3F 5E    1554            CLR     DRCNT2
1585 3F 5F    1555            CLR     REG3
1587 3F 60    1556            CLR     REG4
1589 3F 61    1557            CLR     REG5
158B 3F 7A    1558            CLR     THIRD1
158D 3F 7B    1559            CLR     THIRDR
158F 3F 7F    1560            CLR     ERRCNT
1591 3F 6E    1561            CLR     PSTAT2
              1562    ;       LDA     #$10
              1563    ;       STA     PSTAT2
              1564    ;
1593 B6 51    1565            LDA     DSPDG1         ;CHECK RATE VALUE
1595 BA 52    1566            ORA     DSPDG2
1597 BA 53    1567            ORA     DSPDG3
1599 BA 54    1568            ORA     DSPDG4
159B 26 05    1569            BNE     RUNMOT         IF RATE!=0, RUNMOT
              1570    ;       BSET    7,ERRON        ;IT =000 SO SET ERROR BIT
159D 1A 6E    1571            BSET    5,ALRM         ;SET ALARM BIT
159F 10 6D    1572            BSET    0,PSTAT1
              1573    ;       BCLR    0,PSTAT1
15A1 81       1574            RTS                    ;AND RETURN
15A2 12 6D    1575    RUNMOT  BSET    1,PSTAT1       ;MOTOR ON FLAG
15A4 11 6D    1576            BCLR    0,PSTAT1       ;RUN FLAG ON
15A6 1A 01    1577            BSET    5,PORTB        ;MOTOR ON
15A8 81       1578            RTS
              1579    ;
              1580
              1581
              1582    $EJECT
              1583    ;       DOSE CHECK
              1584    ; ---------------------------------
              1585    ;       Conditions
              1586    ;
15A9 05 6D 21 1587    DOSECK  BRCLR   2,PSTAT1,NDOSE ;DON'T DO IF UNIT IS OFF
15AC 00 80 1F 1588            BRSET   0,DSPTST,NDOSE ;DON'T DO IF TEST MODE
15AF 0F 6D 1B 1589            BRCLR   7,PSTAT1,NDOSE ;DON'T DO IF UNIT IS 224
15B2 0E 6F 18 1590            BRSET   7,PSTAT2,NDOSE ;DON'T DO IF ERROR MODE ON
              1591    ;
15B5 00 71 0A 1592            BRSET   0,DFLAG,DOS1   ;IF DOSE FLAG SET THEN DOS1
              1593    ;
15B8 00 76 12 1594            BRSET   0,CWF,NDOSE    ;IF INC OR DEC FLAG PRESSED
15BB 00 77 0F 1595            BRSET   0,CCWF,NDOSE   ;DONT SET UP DOSE FEATURE
              1596    ;
15BE 03 03 0D 1597            BRCLR   1,PORTD,SETDOS ;IF DOSE BUTTON PUSHED THEN
              1598                                   ;INITIALIZE DOSE MODE
15C1 81       1599            RTS                    ;ELSE RETURN
              1600    ;
15C2 3C 57    1601    DOS1    INC     DOSECT
15C4 B6 57    1602            LDA     DOSECT
15C6 A1 1E    1603            CMP     #30
15C8 22 13    1604            BHI     DOS2
15CA CD 14D7  1605            JSR     DOSTST
15CD 81       1606    NDOSE   RTS
              1607    ;
15CE 10 71    1608    SETDOS  BSET    0,DFLAG        ;SET DOSE MODE FLAG
15D0 1D 6E    1609            BCLR    6,VOLM         ;CLEAR VOLUME FLAG
              1610    ;
15D2 01 6D 04 1611            BRCLR   0,PSTAT1,CONDO ;IF PUMP IN HOLD,
15D5 16 6D    1612            BSET    3,PSTAT1       ;SET START FLAG TO DISABLE FLASH
15D7 18 6D    1613            BSET    4,PSTAT1       ;MAKE DISPLAY ON
              1614                                   ;ELSE, JUST CONTINUE WITH DOSE
15D9 3F 57    1615    CONDO   CLR     DOSECT         ;CLEAR DOSE COUNTER
15DB 20 E5    1616            BRA     DOS1           ;CONTINUE DOSE HANDLING
              1617    ;
```

```
15DD CD 1745    1618        DOS2    JSR     DSEXP
15F0 B6 57      1619                LDA     DOSECT
15E2 A1 78      1620                CMP     #120
15E4 25 E7      1621                BLO     NDOSE
15E6 CD 1756    1622                JSR     UPDATE
15E9 11 71      1623                BCLR    0,DFLAG         ;NO DOSE MODE
15EB 3F 57      1624                CLR     DOSECT
15ED 81         1625                RTS
                1626        ;
                1627        $EJECT
                1628        ;
                1629        ;       VOLUME DISPLAY CHECK
                1630        ;---------------------------------------------------------------
                1631        ;       Conditions
                1632        ;
15EE 05 6D 3C   1633        VOLDIS  BRCLR   2,PSTAT1,NVL    ;DONT DO IF OFF
15F1 00 80 39   1634                BRSET   0,DSPTST,NVL    ;DONT DO IF IN TEST MODE
15F4 0F 6D 36   1635                BRCLR   7,PSTAT1,NVL    ;DONT DO IF MODEL 224
                1636        ;       BRSET   0,DFLAG,NVL     ;DON'T DO IF IN DOSE MODE
15F7 0E 6E 33   1637                BRSET   7,ERRON,NVL     ;DON'T DO IF ERROR MODE
15FA 00 76 30   1638                BRSET   0,CWF,NVL       ;DONT DO IF INC OR DEC BUTTON
15FD 00 77 2D   1639                BRSET   0,CCWF,NVL      ;IS PRESSED
                1640        ;
1600 B6 59      1641                LDA     VS1             ;UPDATE CLEAR VOLUME LED.
1602 BA 5A      1642                ORA     VS2
1604 27 04      1643                BEQ     NOVLED
1606 1D 01      1644                BCLR    6,PORTB         ;TURN VOLUME LED OFF IF VOLUME NOT ZERO
1608 20 02      1645                BRA     VOLBUT1
160A 1C 01      1646        NOVLED  BSET    6,PORTB         ;IF NO VOLUME TURN ON LED
                1647        ;
160C 0C 6E 11   1648        VOLBUT1 BRSET   6,VOLM,VOL1     ;IF VOL FLAG SET UPDATE DISPLAY
160F 07 03 01   1649                BRCLR   3,PORTD,SETVOL  ;IF VOL BUTTON PUSHED, INITIALIZE DISPLAY
1612 81         1650                RTS
                1651        ;
1613 1C 6E      1652        SETVOL  BSET    6,VOLM          ;SET VOLUME DISPLAY MODE FLAG
1615 11 71      1653                BCLR    0,DFLAG         ;CLEAR DOSE FLAG
1617 3F 79      1654                CLR     VOLTIM          ;CLEAR VOLUME TIMER
1619 01 6D 04   1655                BRCLR   0,PSTAT1,VOL1   ;IF PUMP IN HOLD MODE,
161C 16 6D      1656                BSET    3,PSTAT1        ;SET START FLAG TO DISABLE FLASH
161E 18 6D      1657                BSET    4,PSTAT1        ;MAKE DISPLAY ON
                1658                                        ;ELSE, JUST CONTINUE VOLUME
                1659        ;
1620 3C 79      1660        VOL1    INC     VOLTIM          ;INCREMENT VOLTIM
1622 B6 79      1661                LDA     VOLTIM
1624 A1 1E      1662                CMP     #30             ;IF ELAPSED TIME IS
1626 22 06      1663                BHI     VOL2            ; > 1.00 S, DISPLAY VOLUME
1628 CD 14C2    1664                JSR     VOLTST          ;ELSE DISPLAY VOLTST
162B 10 75      1665                BSET    0,VFLAG         ;SET VOL TEST DISPLAY FLAG
162D 81         1666        NVL     RTS
                1667        ;
162E A1 78      1668        VOL2    CMP     #120            ;CHECK ELAPSED TIME, ACCA LOADED
                1669                                        ;WITH VOLTIM IN VOL1 ROUTINE
1630 22 08      1670                BHI     ENDVOL          ;IF TIME > 5 SEC, END VOL MODE
                1671        ;
1632 11 75      1672                BCLR    0,VFLAG         ;CLEAR VOL TEST DISPLAY FLAG
                1673        ;
1634 AE 59      1674        VSEXP   LDX     #VS1            ;SET POINTER TO VS1 ADDRESS
1636 CD 19E7    1675                JSR     BCDEXP
1639 81         1676                RTS
                1677        ;
163A CD 1756    1678        ENDVOL  JSR     UPDATE          ;RETURN DISPLAY TO RATE
163D 1D 6E      1679                BCLR    6,VOLM
163F 81         1680                RTS
                1681        ;
                1682        ;
                1683        ;
                1684        ;
                1685        $EJECT
                1686        ;
                1687        ;
                1688        ;
                1689        ;       CHECK CLEAR VOLUME BUTTON
                1690        ;---------------------------------------------------------------
                1691        ;       Conditions
                1692        ;
1640 05 6D 40   1693        CKCLR   BRCLR   2,PSTAT1,NOCLR  ;DONT DO IF OFF
1643 00 80 3D   1694                BRSET   0,DSPTST,NOCLR  ;DONT DO IF IN TEST MODE
1646 0F 6D 3A   1695                BRCLR   7,PSTAT1,NOCLR  ;DONT DO IF MODEL 224
1649 00 83 24   1696                BRSET   0,CKBEP,CNALRM  ;IF ALARM ALREADY SET, HANDLE BEEP
                1697        ;
                1698        ;       Has volume clr button been pressed
                1699        ;
```

```
164C 08 03 35      1700          CLR     BRSET   4,PORTD,NCLR1   ;IF CLR BUTTON NOT PRESSED RETURN
                   1701          ;
                   1702          ;       DEBOUNCE SWITCH
164F 02 73 31      1703                  BRSET   1,HTEST,NOCLR   ;IF BUTTON SENSED LAST CYCLE, MUST BE
                   1704          ;                               ;SAME PULSE SO IGNORE
1652 12 73         1705                  BSET    1,HTEST         ;ELSE SET FLAG FOR NEXT CYCLE
                   1706          ;
1654 0D 6E 2C      1707                  BRCLR   6,VOLM,NOCLR    ;IF NOT VOLUME MODE, RETURN
                   1708          ;
1657 B6 79         1709                  LDA     VOLTIM          ;CHECK VOLTIM
1659 A1 1F         1710                  CMP     #31             ;IF 'VOL' 'DISPLAY STILL ON
165B 23 26         1711                  BLS     NOCLR           ;DON'T CLEAR YET
                   1712          ;
                   1713          ;       CHECK IF OK TO CLEAR VOLUME
                   1714          ;
165D B6 55         1715                  LDA     DS1             ;IF DOSE = 0, CONTINUE CLEAR
165F BA 56         1716                  ORA     DS2
1661 27 1A         1717                  BEQ     CLR1
                   1718          ;
1663 CD 1951       1719                  JSR     CPVTOD          ;IF DOSE != 0 AND DOSE DEL.,
1666 A3 FF         1720                  CPX     #$FF
1668 27 13         1721                  BEQ     CLR1            ;IF X = FF, CONTINUE WITH CLEAR VOL
                   1722          ;                               ;ELSE, ENABLE SHORT ALARM
166A 10 83         1723          CKALRM  BSET    0,CKBEP         ;SET CHECK ALARM BIT TO ENABLE BEEP
166C 3F 84         1724                  CLR     CKTIM           ;INITIALIZE BEEP TIME
166E 1E 01         1725                  BSET    7,PORTB         ;TURN ON ALARM
                   1726          ;
1670 3C 84         1727          CNALRM  INC     CKTIM           ;INCREMENT BEEP TIMER
1672 B6 84         1728                  LDA     CKTIM           ;CHECK IF TIME TO STOP BEEP
1674 A1 05         1729                  CMP     #$05
1676 25 04         1730                  BLO     CONBP           ;IF CKTIM ( AA, CONTINUE BEEP
1678 1F 01         1731                  BCLR    7,PORTB         ;ELSE, TURN OFF BEEP
167A 11 83         1732                  BCLR    0,CKBEP         ;CLEAR CK BEEP FLAG
167C 81            1733          CONBP   RTS
                   1734          ;
                   1735          ;       CLEAR VOLUME
                   1736          ;
167D CD 1941       1737          CLR1    JSR     CLVOL           ;CLEAR VOLUME
1680 CC 1634       1738                  JMP     VSEXP
                   1739          ;
1683 81            1740          NOCLR   RTS
                   1741          ;
1684 13 73         1742          NCLR1   BCLR    1,HTEST
1686 81            1743                  RTS
                   1744          ;
                   1745          $EJECT
                   1746          ;
                   1747
                   1748          ;
                   1749          ;
                   1750          ;       Inputing the rate (model 324)
                   1751          ;       ---------------------------------------------------------
                   1752          ;
                   1753          ;       Conditions
                   1754          ;
1687 05 6D 23      1755          INRATE2 BRCLR   2,PSTAT1,OVER1  ;IF OFF DONT DO
168A 00 6E 20      1756                  BRSET   0,LOWBAT,OVER1  ;DONT DO IF LOWBAT
168D 0E 6E 1D      1757                  BRSET   7,ERRON,OVER1   ;DONT DO IF ERROR MODE
1690 0F 6D 1A      1758                  BRCLR   7,PSTAT1,OVER1  ;IF MODEL 224 DONT DO
1693 00 80 17      1759                  BRSET   0,DSPTST,OVER1  ;DONT DO IF IN TEST MODE
1696 0C 6E 14      1760                  BRSET   6,VOLM,OVER1    ;DONT DO IF IN VOLUME DISPLAY
1699 06 6D 03      1761                  BRSET   3,PSTAT1,CRTE   ;IF IN START MODE DO NOW
169C 01 6D 0E      1762                  BRCLR   0,PSTAT1,OVER1  ;DON'T DO IN RUN MODE
                   1763          ;
                   1764          ;       Check for rate change
                   1765          ;
169F 03 02 12      1766          CRTE    BRCLR   1,PORTC,CCW1    ;IF BUTTON DOWN DO DECREASE
16A2 3F 77         1767                  CLR     CCWF            ;CLEAR FLAG IF NOT DOWN
16A4 01 02 07      1768                  BRCLR   0,PORTC,CW1     ;IF BUTTON DOWN GO INCREASE
16A7 3F 76         1769                  CLR     CWF             ;CLEAR FLAG IF NOT DOWN
16A9 3F 78         1770                  CLR     SPEED1
16AB 3F 7C         1771                  CLR     OUTSPD
16AD 81            1772          OVER1   RTS                     ;RETURN IF NO BUTTONS DOWN
                   1773          ;
                   1774          ;       Set flag to increase the rate
                   1775          ;
16AE 10 76         1776          CW1     BSET    0,CWF           ;SET FLAG FOR RATE INCREASE
16B0 CD 16BA       1777                  JSR     SPEED           ;GO GET SPEED AND UPDATE
16B3 81            1778                  RTS
                   1779          ;
```

```
                1780    ;       Set flag to decrease the rate
                1781    ;
16B4 10 77      1782    CCW1    BSET    0,CCWF          ;SET FLAG FOR RATE DECREASE
16B6 CD 16BA    1783            JSR     SPEED           ;GO SET SPEED AND UPDATE
16B9 81         1784            RTS
                1785    ;
                1786    ;       Speed control for touch panel
                1787    ;
16BA 3C 78      1788    SPEED   INC     SPEED1
16BC B6 78      1789            LDA     SPEED1
16BE A1 40      1790            CMP     #$40            ;WAIT 1.98 SEC
16C0 23 04      1791            BLS     SPD1            ;AT FIRST SPEED
16C2 A1 90      1792            CMP     #$90            ;WAIT 3.465 SEC
16C4 23 15      1793            BLS     SPD2
16C6 A6 F0      1794            LDA     #$F0
16C8 B7 78      1795            STA     SPEED1
16CA 20 21      1796            BRA     SPD4
                1797    ;
                1798    ;       Speed 1
                1799    ;
16CC 3C 7C      1800    SPD1    INC     OUTSPD
16CE B6 7C      1801            LDA     OUTSPD
16D0 A1 0F      1802            CMP     #$0F            ;CHANGE EVERY .495 SEC
16D2 27 19      1803            BEQ     SPD4
16D4 B6 78      1804            LDA     SPEED1          ;EXCEPT FIRST TIME THROUGH
16D6 A1 01      1805            CMP     #$01
16D8 27 13      1806            BEQ     SPD4
16DA 81         1807            RTS
                1808    ;
                1809    ;       Speed 2
                1810    ;
16DB 3C 7C      1811    SPD2    INC     OUTSPD
16DD B6 7C      1812            LDA     OUTSPD
16DF A1 06      1813            CMP     #$06            ;CHANGE EVERY .198 SEC
16E1 27 0A      1814            BEQ     SPD4
16E3 81         1815            RTS
                1816    ;
                1817    ;       Speed 3
                1818    ;
16E4 3C 7C      1819    SPD3    INC     OUTSPD
16E6 B6 7C      1820            LDA     OUTSPD
16E8 A1 05      1821            CMP     #$05
16EA 27 01      1822            BEQ     SPD4
16EC 81         1823            RTS
                1824    ;
16ED 3F 7C      1825    SPD4    CLR     OUTSPD
16EF 16 6D      1826            BSET    3,PSTAT1        ;MAKE START ON
16F1 18 6D      1827            BSET    4,PSTAT1        ;TURN DISPLAY ON
16F3 00 77 06   1828            BRSET   0,CCWF,DEC1     ;IF CCW FLAG SET DEC DOSE OR RATE
                1829    ;                               ;ELSE INCREASE DOSE OR RATE
                1830    ;       INCREASE
                1831    ;
16F6 00 71 09   1832            BRSET   0,DFLAG,INCR1D  ;IF DOSE, INCREMENST DOSE
16F9 CC 131E    1833            JMP     INCR1           ;ELSE, INCREMENT RATE
                1834    ;
                1835    ;       DECREMENT
                1836    ;
16FC 00 71 28   1837    DEC1    BRSET   0,DFLAG,DECR1D  ;IF DOSE, DECREMENT DOSE
16FF CC 1365    1838            JMP     DECR1           ;ELSE, DECREMENT RATE
                1839    ;
                1840
1702 B6 57      1841    INCR1D  LDA     DOSECT          ;DELAY INC TO ALLOW doSE DISPLAY
1704 A1 1F      1842            CMP     #31
1706 23 42      1843            BLS     NODOSE          ;RETURN FROM INC
1708 15 71      1844            BCLR    2,DFLAG         ;CLR DOSE 0 FLAG
170A A6 3D      1845            LDA     #61             ;RESET DOSE TIMER EACH
170C B7 57      1846            STA     DOSECT          ;TIME BUTTON IS PRESSED
                1847    ;
170E B6 56      1848            LDA     DS2             ;IF DOSE IS 2000 DONT INCREMENT
1710 A4 F0      1849            AND     #$F0            ;MASK LOWER NIBBLE TO GET MSP
1712 A1 20      1850            CMP     #$20
                1852
1716 B6 55      1853            LDA     DS1
1718 AB 05      1854            ADD     #$05            ;BINARY ADD DS1
171A 8D         1855            DAA                     ;CONVERT TO BCD
171B B7 55      1856            STA     DS1
171D B6 56      1857            LDA     DS2
171F A9 00      1858            ADC     #$00            ;BINARY ADD CARRY
1721 8D         1859            DAA                     ;CONVERT TO BCD
1722 B7 56      1860            STA     DS2
```

```
1724 CC 1745    1861            JMP     DSEXP           ; UPDATE DOSE
                1862    ;
                1863    ;       DECREMENT DOSE BY 1
                1864
1727 B6 57      1865    DECR1D  LDA     DOSECT          ;DELAY INC TO ALLOW doSE DISPLAY
1729 A1 1F      1866            CMP     #31
172B 23 1D      1867            BLS     NODOSE          ;RETURN FROM INC
172D A6 3D      1868            LDA     #61             ;RESET DOSE TIMER
172F B7 57      1869            STA     DOSECT          ;EACH TIME BUTTON IS PUSHED
                1870    ;
1731 B6 55      1871            LDA     DS1             ;IF DOSE IS 0 DONT DECREMENT
1733 BA 56      1872            ORA     DS2
1735 27 13      1873            BEQ     NODOSE
                1874
                1875    ;
1737 B6 55      1876            LDA     DS1
1739 AB 95      1877            ADD     #$95            ;10 COMPLIMENT BINARY SUBTRACT
173B 8D         1878            DAA                     ;CONVERT RESULT TO BCD
173C B7 55      1879            STA     DS1
173E B6 56      1880            LDA     DS2
1740 A9 99      1881            ADC     #$99            ;10 COMPLIMENT BINARY SUBTRACT WITH C
1742 8D         1882            DAA                     ;CONVERT TO BCD
1743 B7 56      1883            STA     DS2
                1884    ;
1745 AE 55      1885    DSEXP   LDX     #DS1            ;SET POINTER TO DS1 ADDRESS
1747 CD 19E7    1886            JSR     BCDEXP
174A 81         1887    NODOSE  RTS
                1888    ;
                1889    ;
                1890    ;----------- TOGGLE DIGIT ONE -----------------------
                1891    ;
                1892    ;
                1893    ;
174B 00 51 05   1894    TOGGLE  BRSET   0,DSPDG1,DEC5   ;IF 5 MAKE 0
174E A6 05      1895            LDA     #$05            ;IF 0 MAKE 5
1750 B7 51      1896            STA     DSPDG1
1752 81         1897            RTS
1753 3F 51      1898    DEC5    CLR     DSPDG1          ;
1755 81         1899            RTS
                1900    ;
                1901    ;
                1902    ;       Update the digit numbers
                1903    ;
                1904    ;
1756 BE 51      1905    UPDATE  LDX     DSPDG1
1758 D6 101F    1906            LDA     DIGITS,X
175B B7 50      1907            STA     SAMPL4
175D BE 52      1908            LDX     DSPDG2
175F D6 101F    1909            LDA     DIGITS,X
1762 B7 4F      1910            STA     SAMPL3
1764 BE 53      1911            LDX     DSPDG3
1766 D6 101F    1912            LDA     DIGITS,X
1769 B7 4E      1913            STA     SAMPL2
176B BE 54      1914            LDX     DSPDG4
176D D6 101F    1915            LDA     DIGITS,X
1770 B7 4D      1916            STA     SAMPL1
                1917    ;CHECK THIS CODE FOR HANDLING ZEROST FLAG
                1918    ;
1772 1D 74      1919            BCLR    6,ZEROST        ;INITIALIZE ZEROST
1774 1F 74      1920            BCLR    7,ZEROST        ;AND
1776 3F 64      1921            CLR     COUNT3          ;COUNT3 FOR LED MUX ROUTINE
                1922
                1923    ;
1778 3F 4B      1924            CLR     HLDTM1          ;CLEAR HLDTIM1 AND HLDTIM2
177A 3F 4C      1925            CLR     HLDTM2          ;TO RESTART 2 1/2 MIN TIMER
                1926                                    ;EACH TIME DISPLAY IS UPDATED
                1927    ;
                1928    ;
                1929    ;               CALCULATE MOTOR TIMES
                1930    ;
177C 3F 67      1931            CLR     QH
177E 3F 69      1932            CLR     PH
1780 A6 0A      1933            LDA     #10
1782 B7 68      1934            STA     QL
1784 B6 52      1935            LDA     DSPDG2
1786 B7 6A      1936            STA     PL
1788 CD 196F    1937            JSR     MULT16
178B B6 51      1938            LDA     DSPDG1
178D BB 68      1939            ADD     QL
178F B7 46      1940            STA     ALGO
```

```
1791 A6 64      1941            LDA     #100
1793 B7 68      1942            STA     QL
1795 B6 53      1943            LDA     DSPDG3
1797 B7 6A      1944            STA     PL
1799 CD 196F    1945            JSR     MULT16
179C B6 46      1946            LDA     ALGO
179E B7 6A      1947            STA     PL
17A0 CD 1962    1948            JSR     ADD16
17A3 B6 67      1949            LDA     QH
17A5 B7 69      1950            STA     PH
17A7 B6 68      1951            LDA     QL
17A9 B7 6A      1952            STA     PL
17AB A6 D6      1953            LDA     #$D6
17AD B7 67      1954            STA     QH
17AF A6 E8      1955            LDA     #$E8
17B1 B7 6A      1956            STA     QL
                1957            JSR     DIV16
17B6 B6 53      1958            LDA     DSPDG3
17B8 26 09      1959            BNE     MULT3
17BA B6 65      1960            LDA     XH
17BC B7 48      1961            STA     TIMHI
17BE B6 66      1962            LDA     XL
17C0 B7 47      1963            STA     TIMLO
17C2 81         1964            RTS
                1965    ;
17C3 B6 65      1966    MULT3   LDA     XH
17C5 B7 67      1967            STA     QH
17C7 B6 66      1968            LDA     XL
17C9 B7 68      1969            STA     QL
17CB A6 03      1970            LDA     #3
17CD B7 6A      1971            STA     PL
17CF 3F 69      1972            CLR     PH
17D1 CD 196F    1973            JSR     MULT16
17D4 B6 68      1974            LDA     QL
17D6 B7 47      1975            STA     TIMLO
17D8 B6 67      1976            LDA     QH
17DA B7 48      1977            STA     TIMHI
17DC 81         1978            RTS
                1979    ;
                1980    ;
                1981    $EJECT
                1982    ;
                1983    ;
                1984    ;               AC OR DC CHECK
                1985    ;-----------------------------------------------------
                1986    ;
17DD 0D 02 03   1987    ACDC    BRCLR   6,PORTC,AC      ;IF CLR ITS AC
17E0 13 6E      1988            BCLR    1,ACON          ;IF NOT CLEAR THE FLAG
17E2 81         1989            RTS
17E3 12 6E      1990    AC      BSET    1,ACON          ;SET FLAG ITS AC
                1991    ;       CLR     T25             ;RESET TIMER FOR AUTO OFF
                1992    ;       CLR     T20
17E5 81         1993            RTS
                1994    ;
                1995    $EJECT
                1996    ;
                1997    ;
                1998    ;               BATTERY CHECK
                1999    ;-----------------------------------------------------
                2000    ;
17E6 02 6E 37   2001    BATCK   BRSET   1,ACON,NOLOB    ;IF ON AC DONT DO
17E9 00 80 45   2002            BRSET   0,DSPTST,NLB    ;DONT DO IF TEST MODE
17EC 00 6E 1D   2003            BRSET   0,LOWBAT,LBTM   ;IF LOW ALREADY TIME 15 MIN.
17EF 03 6D 07   2004            BRCLR   1,PSTAT1,LOBCK  ;IF MOTOR OFF CHECK
17F2 B6 5B      2005            LDA     REG1            ;WAIT UNTILL MOTOR RUNS .4 SEC
17F4 A1 1E      2006            CMP     #30
17F6 22 01      2007            BHI     LOBCK
17F8 81         2008            RTS
17F9 08 02 35   2009    LOBCK   BRSET   4,PORTC,NLB     ;IF NO SIGNAL THEN LOW BAT
17FC 05 6D 1A   2010            BRCLR   2,PSTAT1,KILTIM ;IF PUMP IS OFF, DISABLE PUMP
17FF 10 6E      2011            BSET    0,LOWBAT        ;SET LOW BAT FLAG
1801 1E 6E      2012            BSET    7,ERRON         ;SET ERROR
1803 1A 6F      2013            BSET    5,ALRM          ;SET ALARM
1805 17 6D      2014            BCLR    3,PSTAT1        ;GET OUT OF START MODE TO ENABLE LOW BAT
1807 11 71      2015            BCLR    0,DFLAG         ;CLEAR DOSE MODE FLAG
1809 1D 6F      2016            BCLR    6,VOLM          ;CLEAR VOLUME MODE FLAG
180B 81         2017            RTS
                2018    ;
                2019    ;       INCREMENT 15 MIN TIMER
                2020    ;
```

```
180F  3 47     2021          LBTM    INC     BATTM1          ;INCREMENT BATTERY TIMER: BATM1,BATTM2
1811  26 03    2022                  BNE     CONCNT
1813  3F 48    2023                  INC     BATTM2
1815  B6 48    2024          CONCNT  LDA     BATTM2
1817  A1 07    2025                  CMP     #$07            ;IF BAT TIMER HAS COUNTED 15 MIN
1819  27 01    2026                  BEQ     KILTIM          ;KILL POWER
181B  81       2027                  RTS
181C  9B       2028          KILTIM  SEI                     ;SET INT MASK TO PREVENT TURN-ON
181D  A6 0F    2029                  LDA     #$0F            ;DISABLE PUMP
181F  B7 01    2030                  STA     PORTB
1821  20 F9    2031                  BRA     KILTIM
              2032          ;
1823  01 6E 0F 2033          NOLOB   BRCLR   0,LOWBAT,NLB    ;DONT CLEAR ANY THING IF NO LOW BAT
              2034                                           ;THIS MAINTAINS OTHER ERRORS IF PRESENT
1826  11 6E    2035                  BCLR    0,LOWBAT        ;CLR LOW BAT FLAG
1828  1F 6F    2036                  BCLR    7,ERRON         ;CLR ERROR FLAG
182A  1B 6E    2037                  BCLR    5,ALRM          ;CLR ALARM
182C  1A 6D    2038                  BSET    4,PSTAT1        ;MAKE SURE DISPLAY ON
182E  CD 125A  2039                  JSR     UPDATE          ;UPDATE DISPLAY
1831  CD 1948  2040                  JSR     TIMRST          ;CLEAR TIMER COUNTERS
              2041          ;
              2042          ;       JSR     HOLD            ;COMMENTED OUT TO ALLOW MOTOR TO
              2043          ;                               ;CONTINUE WHEN AC APPLIED.
1831  3F 49    2044          NLB     CLR     BATTM1          ;CLEAR BATTERY TIMERS
1833  3F 4A    2045                  CLR     BATTM2
1835  81       2046                  RTS
              2047          ;
              2048          $EJECT
              2049          ;
              2050          ;               DEAD BATTERY CHECK
              2051          ;
              2052          ;       This routine checks the dead battery signal (portc(7)).
              2053          ;       If this signal is active (portc(7)=0), then the routine
              2054          ;       kills power to the processor.
              2055          ;-----------------------------------------------------------------
              2056          ;
1836  02 6E 14 2057          DBATCK  BRSET   1,ACON,NODBCK   ;DON'T DO IF AC POWERED
1839  03 6D 07 2058                  BRCLR   1,PSTAT1,DEADCK ;IF MOTOR OFF CHECK
183C  B6 5B    2059                  LDA     REG1            ;WAIT UNTILL MOTOR RUNS .4 SEC
183E  A1 1E    2060                  CMP     #30
1840  22 01    2061                  BHI     DEADCK
1842  81       2062                  RTS
              2063          ;
1843  0E 02 07 2064          DEADCK  BRSET   7,PORTC,NODBCK  ;IF NO DEAD BAT SIGNAL, RETURN
              2065          ;
1846  9B       2066          DBKIL   SEI                     ;SET INT MASK TO PREVENT TURN-ON
1847  A6 0F    2067                  LDA     #$0F            ;DISABLE PUMP
1849  B7 01    2068                  STA     PORTB
184B  20 F9    2069                  BRA     DBKIL           ;LOOP UNTIL POWER DISSIPATES
              2070          ;
184D  81       2071          NODBCK  RTS
              2072          ;
              2073          $EJECT
              2074          ;
              2075          ;               ALARM
              2076          ;-----------------------------------------------------------------
              2077          ;       Conditions
              2078          ;
184E  05 6D 08 2079          ALARM   BRCLR   2,PSTAT1,NOALM  ;IF OFF DONT ALARM
1851  0C 6E 05 2080                  BRSET   6,VOLM,NOALM    ;IF IN VOLUME DONT DO
1854  0A 6E 03 2081                  BRSET   5,ALRM,ALRMRT   ;IF ALARM FLAG SET THEN ALARM
              2082          ;
              2083          ;
1857  1F 01    2084          ALCLR   BCLR    7,PORTB         ;SET ALARM HIGH
1859  81       2085          NOALM   RTS
185A  08 6D FA 2086          ALRMRT  BRSET   4,PSTAT1,ALCLR
185D  1E 01    2087                  BSET    7,PORTB
185F  81       2088                  RTS
              2089          ;
              2090          $EJECT
              2091          ;
              2092          ;
              2093          ;
              2094          ;               BLINK THE DISPLAY
              2095          ;-----------------------------------------------------------------
              2096          ;
              2097          ;       Conditions
              2098          ;
1860  05 6D 26 2099          BLINK   BRCLR   2,PSTAT1,NOBLIN ;IF OFF DONT DO
1863  06 6D 23 2100                  BRSET   3,PSTAT1,NOBLIN ;DONT BLINK IF START ON
1866  0E 6E 03 2101                  BRSET   7,ERRON,BL1     ;GO BLINK IF ERROR MODE
```

```
1869 01 6D 35    2102            BRCLR   0,PSTAT1,DOTBL  ;DONT BLINK IN RUN
                 2103        ;
                 2104        ;       Blink
                 2105        ;
186C A6 C0       2106   BL1   LDA     #$C0             ;BLANK 4TH DIGIT
186E B7 4D       2107         STA     SAMPL1
1870 09 6D 17    2108         BRCLR   4,PSTAT1,SETBL   ;IF DISPLAY ON BLANK
1873 19 6D       2109         BCLR    4,PSTAT1
1875 0F 6E 11    2110         BRCLR   7,ERRON,NOBLIN
1878 00 6E 5A    2111         BRSET   0,LOWBAT,LO1     ;IF LO BAT ON THEN DO
187B 08 6E 71    2112         BRSET   4,NOSET,NO1      ;IF NO SET THEN DO
187E 04 6E 50    2113         BRSET   2,NDROP,FLO1     ;IF FLOW ERR THEN DO
1881 00 70 45    2114         BRSET   0,DOSER,DOSE1    ;IF DOSE ERROR THEN DO
1884 06 6E 46    2115         BRSET   3,HOLDER,HLD1    ;IF HOLD ERROR THEN DO
1887 20 59       2116         BRA     ERR1
1889 81          2117   NOBLIN RTS
                 2118        ;
                 2119        ;       Hold mode blink
                 2120        ;
188A 18 6D       2121   SETBL BSET    4,PSTAT1          ;BLANK DISPLAY
188C 0F 6E FA    2122         BRCLR   7,ERRON,NOBLIN
188F 00 6E 54    2123         BRSET   0,LOWBAT,BAT1    ;GO DO BAT IF LO BAT
1892 08 6E 5E    2124         BRSET   4,NOSET,SET2     ;GO DO SET IF NO SET
1895 04 6E 4A    2125         BRSET   2,NDROP,ERR1     ;GO DO ERR IF FLOW ERR
1898 00 70 26    2126         BRSET   0,DOSER,OUT2     ;GO DO DEL IF DOSE ERR
189B 06 6E 44    2127         BRSET   3,HOLDER,ERR1    ;GO DO ERR IF HOLD ERR
189E 20 3E       2128         BRA     SYS1
18A0 81          2129         RTS
                 2130        ;
                 2131        ;       Blink the DP during the run mode
                 2132        ;
18A1 BE 63       2133   DOTBL LDX     COUNT2           ;GET DP #
18A3 E6 4D       2134         LDA     SAMPL1,X         ;GET NEW DIGIT
18A5 AA 80       2135         ORA     #$80             ;CLEAR DP
18A7 E7 4D       2136         STA     SAMPL1,X         ;STORE IT FOR DISPLAY
18A9 5C          2137         INCX                     ;BUMP POINTER TO NEXT DIGIT
18AA A3 04       2138         CPX     #$04             ;DONE ALL THREE
18AC 27 09       2139         BEQ     NEWX             ;RESET IF SO
18AE E6 4D       2140   DOTON LDA     SAMPL1,X         ;GET NEXT DIGIT
18B0 A4 7F       2141         AND     #$7F             ;TURN DP ON
18B2 E7 4D       2142         STA     SAMPL1,X         ;STORE IT FOR DISPLAY
18B4 BF 63       2143         STX     COUNT2           ;SAVE COUNT
18B6 81          2144         RTS
                 2145        ;
18B7 0F 6D 03    2146   NEWX  BRCLR   7,PSTAT1,DOT24   ;IF 224, SCROLL 3 DIGITS
18BA 5F          2147         CLRX                     ;RESET COUNTER
18BB 20 F1       2148         BRA     DOTON            ;GO TURN ON
                 2149        ;
18BD AE 01       2150   DOT24 LDX     #$01             ;IF THIRD DIGIT
18BF 20 ED       2151         BRA     DOTON            ;ELSE CONTINUE WITH BLINK ROUTINE
                 2152        ;
                 2153        ;       Error messages
                 2154        ;
18C1 A6 8C       2155   OUT2  LDA     #$8C
18C3 B7 40       2156         STA     SAMPL1
                 2157        ;
18C5 AE 16       2158         LDX     #$16             ;DISPLAY ?
18C7 20 2E       2159         BRA     OUTCHR
                 2160        ;
18C9 AE 19       2161   DOSE1 LDX     #$19             ;DISPLAY DOSE
18CB 20 2A       2162         BRA     OUTCHR
                 2163        ;
                 2164        ;
18CD AE 12       2165   HLD1  LDX     #$12             ;POINT TO ERR MESSAGE
18CF 20 26       2166         BRA     OUTCHR           ;GO LOAD UP DIGITS
                 2167        ;
18D1 AE 06       2168   FLO1  LDX     #$06             ;POINT TO FLO MESSAGE
18D3 20 22       2169         BRA     OUTCHR           ;GO LOAD UP DIGITS
                 2170        ;
18D5 AE 00       2171   LO1   LDX     #$00
18D7 CD 18F7     2172         JSR     OUTCHR
18DA 01 6D C4    2173         BRCLR   0,PSTAT1,DOTBL   ;IF IN RUN MODE, UPDATE DP SCROLL
18DD 81          2174         RTS
                 2175        ;
18DE AE 1C       2176   SYS1  LDX     #$1C             ;DISPLAY SYS
18E0 20 15       2177         BRA     OUTCHR
                 2178        ;
                 2179        ;
18E2 AE 09       2180   ERR1  LDX     #$09
18E4 20 11       2181         BRA     OUTCHR
                 2182        ;
```

```
18E6 AE 03       2183          BAT1    LDX     #$03
18E8 CD 1AF7     2184                  JSR     OUTCHR
18EB 01 6D B?    2185                  BRCLR   0,PSTAT1,DOTBL  ;IF IN RUN MODE, UPDATE DP SCROLL
18EE 81          2186                  RTS
                 2187          ;
18EF AE 0C       2188          NO1     LDX     #$0C
18F1 20 04       2189                  BRA     OUTCHR
                 2190          ;
18F3 AE 0F       2191          SET2    LDX     #$0F
18F5 20 00       2192                  BRA     OUTCHR
                 2193          ;
18F7 D6 1000     2194          OUTCHR  LDA     TABLES,X
18FA B7 4E       2195                  STA     SAMPL2
18FC 5C          2196                  INCX
18FD D6 1000     2197                  LDA     TABLES,X
1900 B7 4F       2198                  STA     SAMPL3
1902 5C          2199                  INCX
1903 D6 1000     2200                  LDA     TABLES,X
1906 B7 50       2201                  STA     SAMPL4
1908 81          2202                  RTS
                 2203          ;
                 2204          $EJECT
                 2205          ;
                 2206          ;               HOLD ERROR
                 2207          ;-------------------------------------------------------------
                 2208          ;       Conditions
                 2209          ;
1909 05 6D 21    2210          HLDER   BRCLR   2,PSTAT1,NOHE   ;DONT DO IF OFF
190C 01 6D 1E    2211                  BRCLR   0,PSTAT1,NOHE   ;DONT DO IF NOT IN HOLD
                 2212          ;
                 2213          ;       Test for hold error
                 2214          ;
190F 3C 4B       2215                  INC     HLDTM1          ;INCREMENT HOLD COUNTER
1911 26 02       2216                  BNE     CNCNT
1913 3C 4C       2217                  INC     HLDTM2
1915 B6 4C       2218          CNCNT   LDA     HLDTM2          ;CHECK IF 2 1/2 MIN ELAPSED
1917 A1 01       2219                  CMP     #$01
1919 22 0A       2220                  BHI     HLDER1          ;IF HLDTIM2 > 1, HOLDER
191B 27 01       2221                  BEQ     CONCK           ;IF HLDTIM2= 1, CHECK HLDTIM1
191D 81          2222                  RTS                     ;ELSE RETURN
                 2223          ;
191E B6 4B       2224          CONCK   LDA     HLDTM1
1920 A1 27       2225                  CMP     #$27            ;IF HLDTIM1 >= 27, HOLDER
1922 24 01       2226                  BHS     HLDER1
1924 81          2227                  RTS
                 2228          ;
1925 17 6D       2229          HLDER1  BCLR    3,PSTAT1        ;CLEAR START FLAG
1927 16 6F       2230                  BSET    3,HOLDER        ;SET HOLD ERROR FLAG
1929 1A 6E       2231                  BSET    5,ALRM          ;ALARM ON
192B 1E 6E       2232                  BSET    7,ERRON         ;ERROR FLAG ON
192D 81          2233          NOHE    RTS
                 2234          ;
                 2235          $EJECT
                 2236          ;
                 2237          ;               ONE DAY WAIT FOR AUTO OFF
                 2238          ;-------------------------------------------------------------
                 2239          ;       Conditions
                 2240          ;
192E 04 6D 0F    2241          TIM24   BRSET   2,PSTAT1,KEEPON ;IF UNIT ON DONT DO
                 2242          ;
                 2243          ;       24HR TURN OFF
                 2244          ;
1931 3C 45       2245                  INC     T25             ;GET COUNTER
1933 B6 45       2246                  LDA     T25
1935 A1 EF       2247                  CMP     #$EF            ;(EF + 1) = 240 x 6 = 24 HOURS
1937 25 07       2248                  BLO     KEEPON
                 2249          ;
1939 9B          2250          KILLP   SEI                     ;SET INT MASK TO PREVENT TURN-ON
193A A6 0F       2251                  LDA     #$0F            ;DISABLE PUMP
193C B7 01       2252                  STA     PORTB
193E 20 F9       2253                  BRA     KILLP           ;LOOP UNTIL POWER DISSAPTES
                 2254          ;
1940 81          2255          KEEPON  RTS
                 2256          ;
                 2257          ;
                 2258          ;               CLEAR VOLUME SUBROUTINE
                 2259          ;       This routine is called by tim24 and ckclr routines.
                 2260          ;-------------------------------------------------------------
                 2261          ;
1941 3F 58       2262          CLVOL   CLR     DECML1
```

```
1943 3F 59      2263            CLR     VS1
1945 3F 5A      2264            CLR     VS2
1947 81         2265            RTS
                2266    ;
                2267    ;                       CLEAR TIMER COUNTERS
                2268    ;-------------------------------------------------------------------
                2269    ;
1948 3F 40      2270    TIMRST  CLR     TS
194A 3F 41      2271            CLR     T5
194C 3F 42      2272            CLR     T10
194E 3F 43      2273            CLR     T15
1950 81         2274            RTS
                2275    ;                       COMPARE DOSE TO VOLUME
                2276    ;-------------------------------------------------------------------
                2277    ;
                2278    ;       IF VOLUME DELIVERED >= PROGRAMMED DOSE, SET X REGISTOR TO FF
                2279    ;
1951 5F         2280    CPVTOD  CLRX
1952 B6 5A      2281            LDA     VS2
1954 B1 56      2282            CMP     DS2
1956 25 09      2283            BLO     VLTD            ;IF VOLUME < DOSE, CLEAR C
1958 22 06      2284            BHI     VGTD            ;IF VOLUME > DOSE, SET C
                2285    ;                               ;ELSE, CHECK VS1
195A B6 59      2286            LDA     VS1
195C B1 55      2287            CMP     DS1
195E 25 01      2288            BLO     VLTD            ;IF VOLUME < DOSE, CLEAR C
                2289    ;
1960 53         2290    VGTD    COMX                    ;SET X TO FF
1961 81         2291    VLTD    RTS
                2292    ;
                2293    ;
                2294    $EJECT
                2295    ;*********************************************************************
                2296    ;                                                                    *
                2297    ;                                                                    *
                2298    ;                       MATH UTILITIES FOLLOW                        *
                2299    ;                                                                    *
                2300    ;                                                                    *
                2301    ;*********************************************************************
                2302
                2303    ;
                2304    ;*********************************************************************
                2305    ;                                                                    *
                2306    ;  PROGRAM ADDS 2, 16-BIT UNSIGNED BINARY NUMBERS, PRODUCING A 17-BIT *
                2307    ; RESULT.                                                             *
                2308    ;       ENTER WITH:  2, UNSIGNED 16-BIT OPERANDS TO BE ADDED IN       *
                2309    ;                    PH , PL and QH , QL.                             *
                2310    ;       EXIT WITH:   17-BIT RESULT IN:   CARRY , QH, QL               *
                2311    ;                    (QH, QL DESTROYED).                              *
                2312    ;                                                                    *
                2313    ;*********************************************************************
                2314    ;
                2315    ;
1962 B6 68      2316    ADD16   LDA     QL      ;ADD LS BYTES.
1964 BB 6A      2317            ADD     PL
1966 B7 68      2318            STA     QL
1968 B6 67      2319            LDA     QH      ;ADD MS BYTES.
196A B9 69      2320            ADC     PH
196C B7 67      2321            STA     QH      ;16-BIT RESULT IN QH, QL.  OVERFLOW IN CARRY.
                2322    ;
196E 81         2323            RTS
                2324    ;
                2325    ;
                2326    ;
                2327    ;
                2328    ;*********************************************************************
                2329    ;                                                                    *
                2330    ;  PROGRAM MULTIPLIES 2, 16 BIT UNSIGNED BINARY OPERANDS, CREATING A 32-*
                2331    ; BIT UNSIGNED RESULT. (NO OVERFLOW IS POSSIBLE).                     *
                2332    ;       ENTER WITH:  OPERANDS TO BE MULTIPLIED IN:                    *
                2333    ;                                                    QH , QL          *
                2334    ;                                            and     PH , PL          *
                2335    ;       EXIT WITH:   32-BIT RESULT IN:   XH , XL , QH , QL            *
                2336    ;                                                                    *
                2337    ;*********************************************************************
                2338    ;
                2339    ;
196F AE 10      2340    MULT16  LDX     #16     ;LOOP COUNTER.
1971 3F 65      2341            CLR     XH      ;CLEAR UPPER 16 BITS OF 32-BIT ACCUM.
1973 3F 66      2342            CLR     XL
```

```
1975 36 67    2343            ROR   QH      ;CHECK BIT 0 OF QL.
1977 36 68    2344            ROR   QL
1979 24 0C    2345    NXT     BCC   ROTAT   ;IF 0, DON'T ADD, JUST SHIFT.
197B B6 66    2346            LDA   XL      ;OTHERWISE, ADD IN THE CONTENTS OF PH , PL TO
197D BB 6A    2347            ADD   PL      ;XH , XL.
197F B7 66    2348            STA   XL
1981 B6 65    2349            LDA   XH
1983 B9 69    2350            ADC   PH
1985 B7 65    2351            STA   XH
              2352    ;
1987 36 65    2353    ROTAT   ROR   XH      ;SHIFT THE 32-BIT ACCUM. 1 BIT RIGHT.
1989 36 66    2354            ROR   XL
198B 36 67    2355            ROR   QH
198D 36 68    2356            ROR   QL
              2357    ;
198F 5A       2358            DECX          ;DO AGAIN IF NOT DONE WITH ALL 16 BITS.
1990 26 E7    2359            BNE   NXT
              2360    ;
1992 81       2361            RTS           ;OTHERWISE, RETURN WITH RESULT IN XH,XL,QH,QL.
              2362    ;
              2363    ;
              2364    ;*******************************************************************
              2365    ;                                                                  *
              2366    ; PROGRAM PERFORMS THE DIVISION OF 2, 16 BIT UNSIGNED OPERANDS, PRODUC-*
              2367    ; ING A 16 BIT UNSIGNED RESULT:                                    *
              2368    ;                                                                  *
              2369    ;              (QH , QL/ PH , PL) -----)  XH , XL                  *
              2370    ;                                                                  *
              2371    ;         ENTER WITH: 16 BIT DIVISOR IN   PH , PL                  *
              2372    ;                     16 BIT DIVIDEND IN  QH , QL                  *
              2373    ;                                                                  *
              2374    ;         EXIT WITH:  QUOTIENT TRUNCATED TO 16 BITS                *
              2375    ;                         IN XH , XL                               *
              2376    ;         REGISTERS AFFECTED: X, A, COUNT1, TEMPA, TEMPX           *
              2377    ;                     (QH, QL, PH, PL DESTROYED)                   *
              2378    ;                                                                  *
              2379    ;*******************************************************************
              2380    ;
              2381    ;
1993 A6 01    2382    DIV16   LDA   #1
1995 3D 69    2383            TST   PH
1997 2B 0B    2384            BMI   DIV153  ;IF DIVISOR IS LEFT-JUSTIFIED.
1999 4C       2385    DIV151  INCA          ;OTHERWISE, KEEP SHIFTING DIVISOR LEFT
199A 38 6A    2386            ASL   PL      ;UNTIL THE MSB IN PH = 1, OR UNTIL
199C 39 69    2387            ROL   PH      ;16 SHIFTS HAVE BEEN DONE.
199E 2B 04    2388            BMI   DIV153
19A0 A1 11    2389            CMP   #17
19A2 26 F5    2390            BNE   DIV151
19A4 B7 62    2391    DIV153  STA   COUNT1  ;COUNT1 = # SHIFTS REQUIRED +1.
19A6 B6 67    2392            LDA   QH      ;MOVE THE DIVIDEND INTO A, X.
19A8 BE 68    2393            LDX   QL
19AA 3F 67    2394            CLR   QH      ;MAKE WAY FOR THE QUOTIENT.
19AC 3F 68    2395            CLR   QL
19AE BF 6C    2396    DIV163  STX   TEMPX   ;STORAGE FOR THE DIVIDEND AFTER SUBTRACTING
19B0 B7 6B    2397            STA   TEMPA   ;OUT DIVISOR.
19B2 9F       2398            TXA
19B3 B0 6A    2399            SUB   PL      ;TRY SUBTRACTING THE DIVISOR.
19B5 B7 6C    2400            STA   TEMPX
19B7 B6 6B    2401            LDA   TEMPA   ;SAVE THE REMAINDER IN TEMPA, TEMPX.
19B9 B2 69    2402            SBC   PH
19BB B7 6B    2403            STA   TEMPA
19BD BE 6C    2404            LDX   TEMPX
19BF 24 10    2405            BCC   DIV165  ;IF CARRY=0, THEN DIVISOR WAS SMALLER THAN
              2406    ;                     ;DIVIDEND. GO SET THE CURRENT QUOTIENT BIT.
              2407    ;                     ;OTHERWISE, ADD THE DIVISOR BACK IN,
19C1 9F       2408            TXA
19C2 BB 6A    2409            ADD   PL
19C4 B7 6C    2410            STA   TEMPX
19C6 B6 6B    2411            LDA   TEMPA
19C8 B9 69    2412            ADC   PH
19CA B7 6B    2413            STA   TEMPA   ;AND SAVE IT.
19CC BE 6C    2414            LDX   TEMPX
19CE 98       2415            CLC           ;THE QUOTIENT BIT WILL BE 0.
19CF 20 01    2416            BRA   DIV167
19D1 99       2417    DIV165  SEC           ;THE QUOTIENT BIT WILL BE 1.
19D2 39 68    2418    DIV167  ROL   QL      ;ROTATE THE QUOTIENT LEFT 1 BIT,
19D4 39 67    2419            ROL   QH      ;SHIFTING THE MOST RECENT QUOTIENT BIT
19D6 34 69    2420            LSR   PH      ;INTO THE LSB.
19D8 36 6A    2421            ROR   PL
19DA 3A 62    2422            DEC   COUNT1  ;KEEP GOING UNTIL THE COUNTER=0.
19DC 26 D0    2423            BNE   DIV163
```

```
19DE B6 67    2424              LDA     QH           ;WHEN DONE, MOVE THE RESULT INTO XH, XL.
19E0 B7 65    2425              STA     XH
19E2 B6 68    2426              LDA     QL
19E4 B7 66    2427              STA     XL
              2428       ;
19E6 81       2429              RTS                  ;RETURN.
              2430
              2431       ;*********************************************************************
              2432       ;                                                                    *
              2433       ;                          BCDEXP                                    *
              2434       ;                                                                    *
              2435       ;  PROGRAM CONVERTS 2 BYTE BCD NUMBER POINTED TO BY THE X REGISTOR TO *
              2436       ;  A 4 BYTE DECIMAL NUMBER. THE FOUR BYTE NUMBER IS CONVERTED ON THE FLY *
              2437       ;  TO THE CORRECT LED DISPLAY SEGMENT CODE WHICH IS SENT TO THE DISPLAY *
              2438       ;  BY THE LED MUX ROUTINE.                                           *
              2439       ;                                                                    *
              2440       ;            ENTER WITH: ADDRESS OF LOWER BCD BYTE IN X              *
              2441       ;                                                                    *
              2442       ;            EXIT WITH:  LED DISPLAY CODE FOR 4 DECIMAL DIGITS       *
              2443       ;                         IN SAMPL1, SAMPL2, SAMPL3, SAMPL4          *
              2444       ;                                                                    *
              2445       ;            REGISTERS AFFECTED: X, A, SAMPL1 - SAMPL4, TEMPX        *
              2446       ;                                                                    *
              2447       ;*********************************************************************
              2448
19E7 BF 6C    2449       BCDEXP  STX     TEMPX        ;STORE POINTER FOR LATER USE
19E9 F6       2450               LDA     ,X           ;GET LOWER BYTE OF BCD DIGIT
19EA A4 0F    2451               AND     #$0F         ;MASK UPPER NIBBLE
19EC 97       2452               TAX
19ED D6 101F  2453               LDA     DIGITS,X     ;CONVERT DECIMAL TO LED CODE
19F0 B7 50    2454               STA     SAMPL4
              2455       ;
19F2 BE 6C    2456               LDX     TEMPX        ;RESTORE FIRST BCD BYTE
19F4 F6       2457               LDA     ,X
19F5 44       2458               LSRA
19F6 44       2459               LSRA
19F7 44       2460               LSRA
19F8 44       2461               LSRA                 ;PUSH UPPER NIBBLE TO LOWER NIBBLE
19F9 97       2462               TAX
19FA D6 101F  2463               LDA     DIGITS,X     ;CONVERT DECIMAL TO LED CODE
19FD B7 4F    2464               STA     SAMPL3
              2465       ;
19FF 3C 6C    2466               INC     TEMPX        ;SET POINTER TO UPPER BCD DIGIT
1A01 BE 6C    2467               LDX     TEMPX        ;GET SECOND BCD DIGIT
1A03 F6       2468               LDA     ,X
1A04 A4 0F    2469               AND     #$0F         ;MASK UPPER NIBBLE
1A06 97       2470               TAX
1A07 D6 101F  2471               LDA     DIGITS,X     ;CONVERT DECIMAL TO LED CODE
1A0A B7 4E    2472               STA     SAMPL2
              2473       ;
1A0C BE 6C    2474               LDX     TEMPX        ;RESTORE SECOND BCD DIGIT
1A0E F6       2475               LDA     ,X
1A0F 44       2476               LSRA
1A10 44       2477               LSRA
1A11 44       2478               LSRA
1A12 44       2479               LSRA                 ;PUSH UPPER NIBBLE TO LOWER NIBBLE
1A13 97       2480               TAX
1A14 D6 101F  2481               LDA     DIGITS,X     ;CONVERT DECIMAL TO LED CODE
1A17 B7 4D    2482               STA     SAMPL1
              2483       ;
              2484       ;       UPDATE DISPLAY FLAGS USED BY LED MUX
              2485       ;
1A19 1D 74    2486               BCLR    6,ZEROST     ;CLEAR MSD ZERO FLAG
1A1B 1F 74    2487               BCLR    7,ZEROST     ;CLEAR MSD-1 ZERO FLAG
1A1D 3F 64    2488               CLR     COUNT3       ;CLEAR MUX COUNTER
1A1F 81       2489               RTS
              2490       ;
              2491       *EJECT
              2492
     =1C00    2493               ORG     PMPTST
              2494
1C00 1E 01    2495       ELOOP   BSET    7,PORTB
1C02 20 FC    2496               BRA     ELOOP
              2497       ;
              2498               END
```

We claim:

1. A motor unit for a medical fluid delivery system for use with a disposable delivery set for pumping medical fluid, comprising:
   pump operating means, including a motor, for acting in cooperation with said delivery set to deliver a volume of said fluid during each operating cycle;
   pump control means for controlling said pump operating means to deliver said fluid at a desired volumetric rate, said pump control means including means responsive to signals indicating said desired rate for activating said pump operating means for one of said operating cycles and for repeating said activation at variable time intervals selected in accordance with said desired volumetric rate;
   wherein said pump control means includes means for sensing a condition of said pump operating means with respect to said operating cycle; and
   wherein said pump operating means comprises a DC motor and wherein said means for sensing the condition of said pump operating means comprises means for sensing the AC component of the current supplied to said DC motor.

2. A motor unit in accordance with claim 1 wherein said pump operating means comprises a pump rotor for acting in cooperation with a pump tube on said delivery set and wherein said operating cycle comprises a selected angular rotation of said pump rotor.

3. A motor unit in accordance with claim 1 wherein said means for sensing comprises at least one magnet and a magnetic field sensor.

4. In a fluid delivery system comprising a motor unit and a disposable delivery set, wherein said motor unit includes a rotor driven by a DC motor for engaging a flexible pump tube on said delivery set to form a peristaltic pump, a method for controlling the rate of fluid delivery by said system, comprising:
   detecting an AC component of current supplied to said DC motor and forming digital pulses representative thereof;
   operating said motor unit to rotate said rotor until a selected number of said digital pulses occur; and
   repeating said operating step at a time interval selected according to a desired delivery rate of said delivery system.

5. A method in accordance with claim 4 wherein said operating step further includes a step of inhibiting said AC detecting step for a selected time.

6. A motor unit for a medical fluid delivery system for use with a disposable delivery set having a flexible pump tube for engagement with said motor unit for pumping medical fluids, comprising:
   a housing for receiving at least portions of said delivery set;
   a motor mounted on said housing;
   a rotor mounted on said housing and driven by said motor for rotational movement with respect to said housing and for receiving said flexible pump tube for forming a peristaltic pump;
   at least one magnet and at least one magnetic field detector mounted to said rotor and said housing for relative rotational motion with respect to each other, said magnet and said magnetic field detector being operatively adjacent to each other at at least one rotational position of said rotor;
   and pump control means, responsive to selection of a fluid delivery rate and responsive to said magnetic field detector, for operating said motor until said rotor is in said rotational position with said magnet and said magnetic field detector adjacent each other and for repeating said operation at variable time intervals selected in accordance with said selected fluid delivery rate.

7. A motor unit for a medical fluid delivery system for use with a disposable delivery set having a flexible pump tube for engagement with said motor unit for pumping medical fluids, comprising:
   a housing for receiving at least portions of said delivery set;
   a rotor driven by a DC motor, mounted on said housing for rotational motion with respect to said housing and for receiving said flexible pump tube for forming a peristaltic pump;
   means for sensing AC component of the current supplied to said DC motor thereby to sense rotation of said rotor by an incremental amount corresponding to an incremental volume of said pumped fluid;
   and pump control means, responsive to selection of a fluid delivery rate and responsive to said current sensing means, for operating said motor until said incremental rotation is sensed and for repeating said operation at variable time intervals selected in accordance with said selected fluid delivery rate.

8. In a fluid delivery system comprising a motor unit and a disposable delivery set, wherein said motor unit includes a motor driven rotor for engaging a flexible pump tube on said delivery set to form a peristaltic pump, a method for detecting the absence of the pump tube on said rotor, comprising:
   providing current to a DC motor to operate said rotor;
   detecting an AC component of the current provided to said DC motor; and
   comparing the detected AC component of said current to a reference level to detect current variation resulting from the presence of the pump tube on said rotor.

* * * * *